United States Patent
Bates et al.

(10) Patent No.: US 6,521,635 B1
(45) Date of Patent: Feb. 18, 2003

(54) INHIBITION OF MXR TRANSPORT BY ACRIDINE DERIVATIVES

(75) Inventors: Susan Bates, Bethesda, MD (US); Robert Robey, Laurel, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/767,594

(22) Filed: Jan. 22, 2001

Related U.S. Application Data

(60) Provisional application No. 60/177,410, filed on Jan. 20, 2000.

(51) Int. Cl.$^7$ .............................................. A61K 31/435
(52) U.S. Cl. ......................... 514/297; 514/287; 514/33
(58) Field of Search ................................ 514/287, 297, 514/33

(56) References Cited

U.S. PATENT DOCUMENTS

| | | | |
|---|---|---|---|
| 5,604,237 A | | 2/1997 | Dumaitre et al. |
| 2002/0037831 A1 | * | 3/2002 | Tiwari et al. .................. 514/2 |

FOREIGN PATENT DOCUMENTS

| WO | WO92/12132 A1 | 7/1992 |
|---|---|---|
| WO | WO96/11007 A1 | 4/1996 |

OTHER PUBLICATIONS

Allen et al., "The Mouse Bcrp1/Mxr/Abcp Gene: Amplification and Overexpression in Cell Lines Selected for Resistance to Topotecan, Mitoxantrone, or Doxorubicin", (1999) *Cancer Research* 59:4237–4241.

Allikmets et al. "Characterization of the Human ABC Superfamily: Isolation and Mapping of 21 New Genes USing the Expressed Sequence Tags Database" (1998) *Cancer Res.* 58:5337–5339.

Boer and Gekeler "Chemosensitizers in Tumor Therapy: New Compounds Promise Better Efficacy" (1995) *Drugs of the Future* 20:499–509.

Chen et al. "Characterization of Adriamycin–resistant Human Breast Cancer Cells Which Display Overexpression of a Novel Resistance–related Membrane Protein" (1990) *J. Biol. Chem.* 265:10073–10080.

den Ouden et al. "In Vitro Effect of GF120918, A Novel Reversal Agent of Multidrug Resistance, on Acute Leukemia and Multiple Myeloma Cells" (1996) *Leukemia* 10:1930–1936.

Dodic et al. "Synthesis and Activity Against Multidrug Resistance in Chinese Hamster Ovary Cells of New Acridone–4–Carboxamides" (1995) 38: 2418–2426.

Doyle et al. "Expression of a 95 kDa Membrane Protein is associated with Low Daunorubicin Accumulation in Leukaemic Blast Cells" (1998) *Proc. Natl. Acad. Sci. U.S.A.* 95:15665–15670.

Hyafil et al. "In Vitro and In Vivo Reversal of Multidrug Resistance by GF120918, an Acridonecarboxamide Derivative" (1993) *Cancer Res.* 53:4595–4062.

Miyake et al., Molecular Cloning of cDNAs Which Are Highly Overexpressed in Mitoxantrone–Resistant Cells: Demonstration of Homology to ABC Transpoprt Genes, (1999) *Cancer Research* 59:8–13.

Sandor et al. "Future Perspectives for the Development of P–glycoprotein Modulators" (1998) *Drug Resistance Updates* 1:190–200.

Witherspoon et al. "Flow Cytometry Assay of Modulation of P–Glaycoprotein Function in Whole Blood by the Multidrug Resistance Inhibitor GG918" (1996) *Clin. Cancer Res.* 2:7–12.

Zhou et al. "Effect of the Multidrug Inhibitor GG918 on Drug Sensitivity of Human Leukemic Cells" (1997) *Leukemia* 11:1516–1522.

* cited by examiner

*Primary Examiner*—James H. Reamer
(74) *Attorney, Agent, or Firm*—Townsend and Townsend and Crew LLP

(57) ABSTRACT

This invention provides methods that are useful for inhibiting a MXR transporter in a cell overexpressing a MXR gene but not overexpressing a Pgp gene by contacting the cell with an acridine derivative. The invention also provides for a method of treating a mammal suffering from a cancer, which overexpressing a MXR gene but not overexpress a Pgp gene, by the co-administration of a chemotherapeutic and an acridine derivative.

14 Claims, 5 Drawing Sheets

INHIBITION OF MXR TRANSPORT BY ACRIDINE DERIVATIVES

CROSS-REFERENCES TO RELATED APPLICATIONS

This application claims the benefit of U.S. Provisional Patent application Ser. No. 60/177,410, filed on Jan. 20, 2000, the teachings of which are herein incorporated by reference.

STATEMENT AS TO RIGHTS TO INVENTIONS MADE UNDER FEDERALLY SPONSORED RESEARCH AND DEVELOPMENT

Not applicable.

FIELD OF THE INVENTION

This invention relates to the field of modulating the transport of compounds from a cell through a membrane protein. More specifically, the invention relates to modulating the transport of compounds from a cell that overexpresses a MXR gene, but does not overexpress a Pgp gene, with an acridine derivative. The invention also relates to the treatment of a mammal suffering from a cancer that overexpresses a MXR gene but does not overexpress a Pgp gene through the co-administration of an acridine derivative and a chemotherapeutic. The acridine derivatives cited in this invention were previously reported to inhibit MDR-1. Surprisingly these acridine derivatives also inhibit MXR as well. Thus, the acridine derivatives cited in this invention are useful as multi-specific antagonists against cells displaying a MDR phenotype.

BACKGROUND OF THE INVENTION

Cancer is a leading cause of death (Ihde and Longo, in Chapter 63 of *Harrison s Principles of Internal Medicine*, 14th edition (1998) (Fauci et al., eds.). In the United States over a half-million people die each year from cancer, accounting for over 20% of all deaths. Cancer is already the leading cause of death in Japan and is expected to be the leading cause of death in the United States sometime next century. Some progress has been made in the treatment of cancers with the use of chemotherapeutic drugs. Antitumor activities have been identified in drugs classes such as antimetabolites, plant alkaloids, topoisomerase inhibitors, and alkylating agents (Slapak and Kufe, in Chapter 86 of *Harrison's Principles of Internal Medicine* (1998)).

Unfortunately, cells and tumors often become resistant to drugs and chemotherapeutics during treatment (Slapak and Kufe, supra). Cells and tumors that have been exposed to a single agent become resistant to the agent's effects (e.g., cytotoxicity). Moreover, cells that become resistant to the treatment of a single agent, such as a cytotoxic chemotherapeutic, often are also resistant to compounds that are unrelated structurally or functionally. This phenomenon is known as multi-drug resistance (MDR). Some studies suggest there is a poor prognosis for patients suffering from certain cancers, whose tumors exhibit the MDR phenotype.

MDR phenotypes are encountered with drugs such as anthracyclines, vinca alkaloids, epipodophyllotoxins, and taxanes. There appear to be several mechanisms for single-agent drug resistance: increased efflux of the drug from the cell, decreased amounts of activating enzyme, increased drug inactivation, increased amounts of target enzyme and an alteration in the drug target (Slapak and Kufe, supra). The mechanisms for the increased efflux of drug from the cell appear to arise from the overexpression of membrane proteins that can transport the chemotherapeutic out of the cell. Cells displaying a MDR phenotype exhibit energy dependent efflux of the drug out of the cell.

Molecular cloning efforts have begun to define the genes encoding the membrane proteins responsible for the MDR phenotypes. All of the genes identified so far belong to a superfamily of proteins known as the ATP-binding cassette proteins (the ABC transporters). One such membrane transporter is P-glycoprotein (Pgp) or MDR (see generally Gottesman and Pastan, (1993) *Annu. Rev. Biochem.* 62: 385–427). The gene for Pgp has been cloned and confers a MDR phenotype when overexpressed in cells. (Gros et al. (1986) *Nature* 323: 728–731; Ueda et al. (1987) *Proc. Natl. Acad. Sci. U.S.A.* 84: 3004–3008; Guild et al. (1988) *Proc. Natl. Acad. Sci. U.S.A.* 85: 1595–1599; Pastan et al. (1988) *Proc. Natl. Acad. Sci. U.S.A.* 85: 4486–4490). In humans, the MDR1 gene (Chen et al. (1986) *Cell* 47: 381–389) can mediate multidrug resistance, whereas the function of the human MDR2 gene is unknown (Gottseman and Pastan, supra). The murine genes that correspond to the human MDR1 are mdr1a (Gros et al. (1986) *Cell* 47: 371–380) and mdr1b (Gottesman and Pastan, supra). Pgp substrates include the epipodophyllotoxins (e.g., etoposide and teniposide) and the anthracyclines (e.g., doxorubicin and daunorubicin) (Devita et al. eds., (1997) *Cancer: Principles and Practice of Oncology*, Section 11). Another gene conferring multi-drug resistance, the multidrug resistance associated protein (MRP) has also been cloned. (U.S. Pat. Nos. 5,489,519 and 5,994,130). MRP has the ability to transport chemotherapeutics such as doxorubicin, vincristine, etoposide and colchicine (Devita et al., supra).

While Pgp and MRP are the most extensively studied drug resistance transporters, the number of newly reported genes suggests the potential involvement of many others in clinical resistance (Gottesman, and Pastan, supra; Loe et al. (1996) *Eur. J. Cancer* 32A 945–957). The canalicular multispecific organic anion transporter (cMOAT or MRP2), responsible for hepatic transport of bilirubin glucuronide, has been correlated with resistance to cisplatinum and to SN38, the active metabolite of CPT-11 (Koike et al. (1997) *Cancer Res.* 57: 5475–5479). A number of MRP and cMOAT homologues (MRP3, MRP4, MRPS, MRP6) have been described (Kool et al. (1997) *Cancer Res.* 57: 3537–3547; Lee et at. (1998) *Cancer Res.* 58: 2741–2747). Examination of an EST database has revealed evidence of 21 previously unknown ABC transporter genes (Allikmets et al. (1996) *Hum. Mol. Genet.* 5: 1649–1655).

More recently, another member of the ABC transporter family was identified in sublines of cells which do not overexpress MDR or MRP. This new member of the ABC transporter family confers a MDR phenotype and is known as MXR, BRCP, or ABCP. The breast cancer resistance gene (BCRP) was identified in an Adriamycin-resistant subline of MCF-7 cells (Doyle et al. (1998) *Proc. Natl. Acad. Sci. U.S.A.* 95: 15665–15670). The mitoxantrone-resistance gene (MXR) was identified in the same subline of MCF-7 cells and in a mitoxantrone-resistant subline of human colon carcinoma cells (Miyake et al. (1999) *Cancer Res.* 59: 8–13). Both genes are almost identical to ABCP, an ABC transporter gene cloned from human placenta (Allikmets et al. (1998) *Cancer Res.* 58: 5337–5339). Homologies with other genes such as the white eye pigment gene suggest that BCRP/MXR/ABCP encodes a protein which is a half-transporter molecule requiring dimerization for function (Croop et al. (1997) *Gene* 185: 77–85; Ewart and Howells (1998) *Methods in Enzymology* 292: 213–224).

Cell lines overexpressing MXR have resistance to mitoxantrone, anthracyclines, topotecan, and the active metabolite of irinotecan, SN38 (Miyake et al., supra). Mitoxantrone is an antineoplastic anthracenedione topoisomerase inhibitor that is used in the treatment of cancers, such as prostate cancer, acute lymphocytic leukemia, breast cancer, and non-Hodgkin's lymphoma. (Slapak and Kufe, supra; *Physicians' Desk Reference*, 53d edition (1999) pp. 1401–1404). Topotecan, a semi-synthetic analog of campothecin, is also a topoisomerase I inhibitor and is used in the treatment of cancers, such as ovarian carcinoma (*Physicians' Desk Reference*, 53d edition (1999) pp. 3058–3061).

Cells transfected with the BCRP/MXA/ABCP gene display reduced rhodamine retention and display a resistance pattern similar to cells which overexpress MXR (Doyle et al., supra). While this is a broad resistance pattern, several notable exceptions include the vinca alkaloids, taxanes and VP-16 (etoposide).

The sensitivity of MDR cells to cytotoxic chemotherapeutic drugs can be restored or reversed if the cells are treated with drugs that block the efflux through the multidrug transporters. Some drugs known as chemosensitizers or reversal agents (e.g., cyclosporin) are known to block the efflux of chemotherapeutic drugs through Pgp and restore sensitivity to chemotherapeutic drugs. An acridine derivative, GF120918 (N-{4-[2-1,2,3,4-tetrahydro-6,7-dimethoxy-2-isoquinolinyl)-ethyl]-phenyl}-9,10-dihydro-5-methoxy-9-oxo-4-acridine carboxamide) (Dumaitre and Dodic, WO 92/12132; Dumaitre and Dodic, U.S. Pat. No. 5,604,237; Dodic et al. (1995) 38: 2418–2426) has been reported to inhibit Pgp-mediated efflux at nanomolar concentrations (Hyafil et al. (1993) *Cancer Res.* 53: 4595–4062; Boer and Gekeler (1995) *Drugs of the Future* 20: 499–509; den Ouden et al. (1996) *Leukemia* 10: 1930–1936; Zhou et al. (1997) *Leukemia* 11: 1516–1522). Pharmaceutical compositions for the administration of GF120918 and GF120918A, the hydrochloride salt of GF120918, are described in Tong et al., WO 96/11007). GF120918 is a Pgp antagonist identified for its potency in reversing Pgp-mediated resistance (Boer and Gekeler (1995) *Drugs of the Future* 20: 499–509; Witherspoon et al. (1996) *Clin. Cancer Res.* 2: 7–12). GF120918 is one of several agents developed as "second generation" Pgp antagonists: compounds with little inherent toxicity which are able to antagonize drug efflux at nanomolar concentrations. GF120918 has been tested in phase I clinical trials and was confirmed to have little toxicity (Witherspoon et al., supra). Using inhibition of rhodamine efflux from circulating CD56+ cells as a surrogate marker for Pgp antagonism, GF120918 was shown in these phase I studies to inhibit Pgp at doses readily achievable in patients (Witherspoon et al., supra).

The development of antagonists against Pgp-mediated drug efflux led to a large number of clinical trials attempting the reversal of drug resistance (Raderer and Scheithauer (1993) *Cancer* 72: 3553–63; Ferry et al. (1996) *Eur. J Cancer* 32A: 1070–1081). Yet, despite the relative ease of sensitizing cells to chemotherapy in the laboratory, clinical trials have been disappointing, with no clear support emerging for the use of chemosensitizers in clinical practice (Sandor et al. (1998) *Drug Resistance Updates* 1: 190–200). One explanation commonly given for the failure of Pgp reversal studies to achieve significant clinical benefit is the presence of other mechanisms of drug resistance. The cloning of new transporters would support this contention. Thus, given the array of ABC transporters (over 200 transporters are predicted for human cells (Ling (1997) *Cancer Chemother. Pharmacol.* 40: S3–S8)) which may play a role in clinical drug resistance, a multispecific antagonist that is able to inhibit more than one transporter or MDR phenotype would be advantageous.

SUMMARY OF THE INVENTION

This invention provides for a method of inhibiting a MXR transporter in a cell overexpressing a MXR gene. Optionally the cell is not overexpressing a Pgp gene. The method involves contacting a cell, which overexpresses a MXR gene, but does not overexpress a Pgp gene, with a compound of formula (I) or salts and solvates thereof:

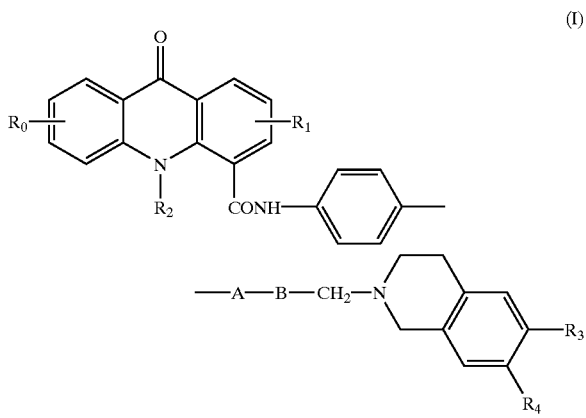

In the general formula above, the symbol $R_0$ represents a hydrogen or halogen atom, or a $C_{1-4}$ alkyl, $C_{1-4}$ alkoxy, $C_{1-4}$ alkylthio, amino, or nitro group. The symbol $R_1$ represents a hydrogen or halogen atom, or a $C_{1-4}$ alkyl, $C_{1-4}$ alkoxy, or $C_{1-4}$ alkylthio group. The symbol $R_2$ represents hydrogen or a $C_{1-4}$ alkyl group. The symbol A represents an oxygen or a sulfur atom or a bond. B represents an unsubstituted $C_{1-4}$ alkylene chain. The symbols $R_3$ and $R_4$ each independently represent a $C_{1-4}$ alkoxy group. The compound of formula (I) or a salt or solvate thereof is present in an amount sufficient to inhibit a MXR transporter.

In a presently preferred embodiment, the compound is N-{4-[2-1,2,3,4-tetrahydro-6,7-dimethoxy-2-isoquinolinyl)-ethyl]-phenyl}-9,10-dihydro-5-methoxy-9-oxo-4-acridine carboxamide or salts and solvates thereof.

In another aspect, the present invention provides a method of assaying the modulation of the functional effect of a test compound on a cell, that overexpresses a MXR gene. Optionally the cell does not overexpress a Pgp gene by an acridine derivative. The method involves contacting a test compound with said cells which overexpress a MXR gene and do not overexpress a Pgp gene, in the presence and absence of an acridine derivative or its salts and solvates thereof; and measuring the ability of the acridine derivative or its salts and solvates thereof, to modulate the functional effect of the test compound. In a presently preferred embodiment, the acridine derivative is N-{4-[2-1,2,3,4-tetrahydro-6,7-dimethoxy-2-isoquinolinyl)-ethyl]-phenyl}-9,10-dihydro-5-methoxy-9-oxo-4-acridine carboxamide or salts and solvates thereof. In some embodiments, the cell has been transfected with a MXR gene or the cell contains a functional MXR gene placed in an expression cassette.

Also provided by the present invention is a method of treatment of a mammal which is suffering from a cancer that overexpresses the MXR gene. Optionally the cell does not overexpress a Pgp gene. The method involves co-administering to a mammal a chemotherapeutic which is recognized by a MXR transporter and an effective amount of an acridine derivative or salts or solvates thereof. In some embodiments, the acridine derivative is N-{4-[2-1,2,3,4-tetrahydro-6,7-dimethoxy-2-isoquinolinyl)-ethyl]-phenyl}-9,10-dihydro-5-methoxy-9-oxo-4-acridine carboxamide, or its salts and solvates thereof.

DEFINITIONS

Figure 1A:
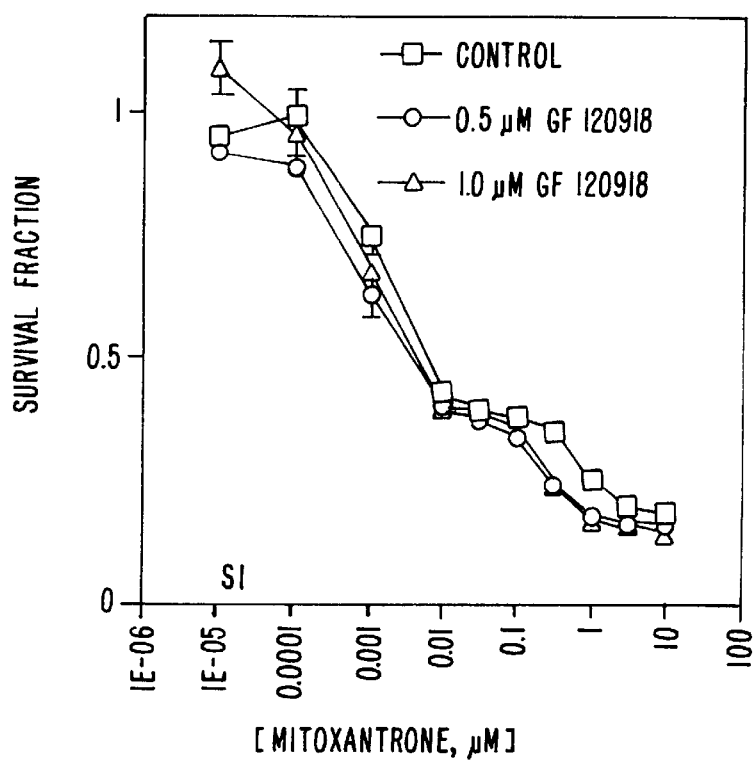
FIG. 1 illustrates the effect of GF120918 on mitoxantrone cytotoxicity in resistant cell lines. Cytotoxicity curves were generated for (A) S1 parental cells, (B) S1-B1-20 Pgp-overexpressing cells, (C) S1-M1-80 cells overexpressing a putative mitoxantrone transporter, and (D) MCF-7 parental cells with mitoxantrone alone (open squares), or with 0.5 μM (open circles) or 1 μM GF120918 (open triangles).
Figure 1B:
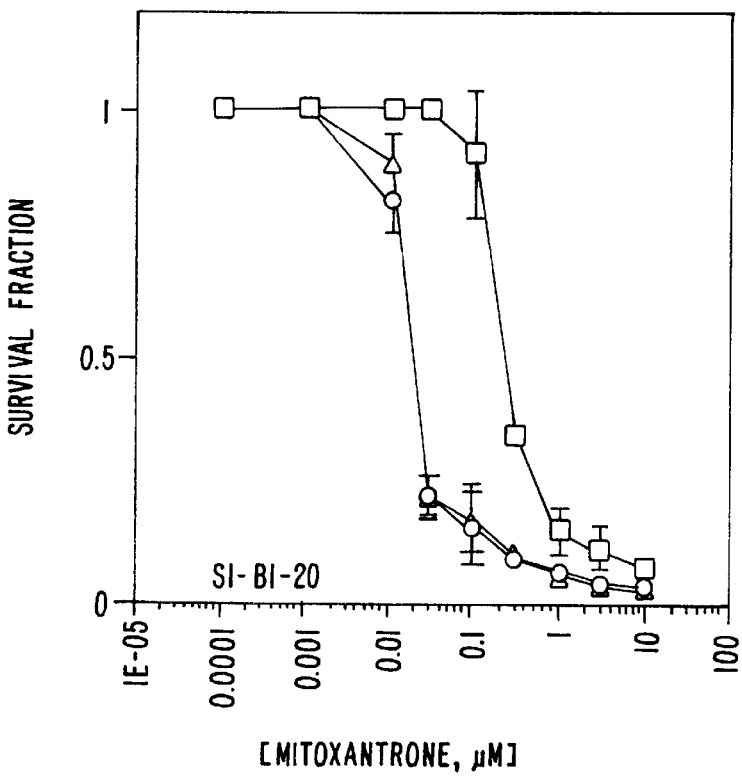
Figure 1C:
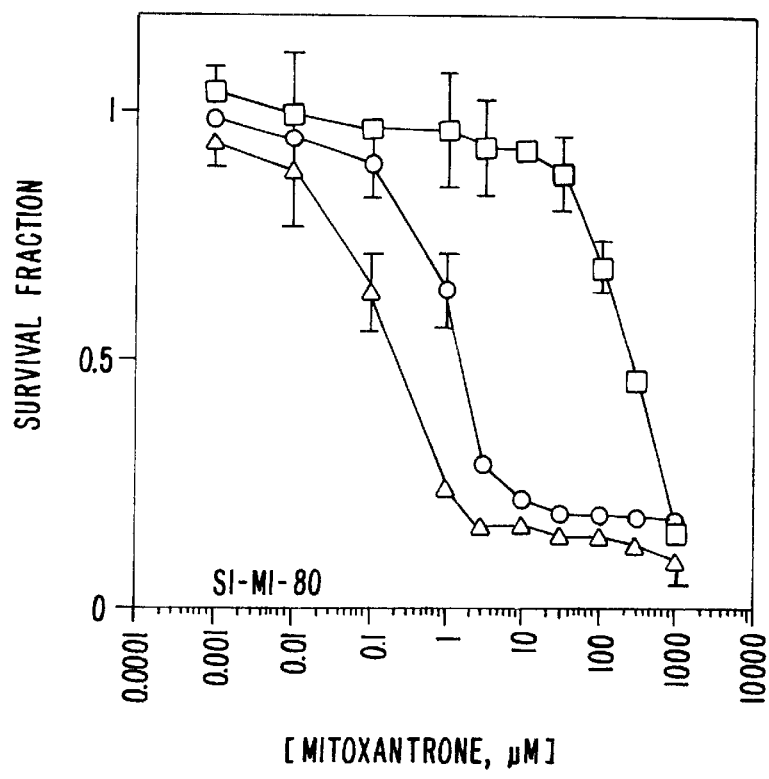

As used herein, the following terms have the meanings ascribed to them unless specified otherwise.

The term "MXR gene" refers to a gene encoding a polypeptide with at least 80% amino acid identity to SEQ ID NO: 1. MXR is the mitoxantrone resistance gene and is also known as BRCP, and ABCP.

The term "Pgp gene" refers to a gene encoding a polypeptide with at least 80% amino acid identity to SEQ ID NO: 2. Pgp is an abbreviation for P-glycoprotein, a member of the ABC transporter superfamily.

The phrase "inhibiting a MXR transporter" refers to a diminution in the efflux of a compound from a cell through a MXR transporter, or to an increase in the retention of a compound inside a cell having a MXR transporter, or the increased cytotoxicity of a drug towards a cell having a MXR transporter.

A "cell overexpressing a MXR gene but not overexpressing a Pgp gene" is a cell that produces MXR mRNA or MXR protein in amounts exceeding that normally produced in that cell type, but does not produce Pgp mRNA or protein in amounts exceeding that normally produced in that cell type. Overexpression can result from selective pressure in the media, gene activation of endogenous genes or by addition of exogenous genes. Functionally, such a cell will typically be resistant the effects of mitoxantrone, topotecan, anthracyclines, or SN38, but not resistant to the effects of vinca alkaloids, taxanes or VP-16.

The compound "N-{4-[2-1,2,3,4-tetrahydro-6,7-dimethoxy-2-isoquinolinyl)-ethyl]-phenyl}-9,10-dihydro-5-methoxy-9-oxo-4-acridine carboxamide" is also known as GF120918.

The term "$C_{1-4}$ alkyl" by itself or as part of another substituent refers to a straight or branched chain, or cyclic hydrocarbon radical or combination thereof, which may be fully saturated, mono- or polyunsaturated and can include di- and multivalent radicals, having the number of carbons designated. A "$C_{1-4}$ alkyl" moiety contains one to four carbons. Examples of saturated hydrocarbon alkyl groups include methyl, ethyl, ethyl, n-propyl, isopropyl, n-butyl, t-butyl, isobutyl, sec-butyl, cyclopropylmethyl, homologs and isomers thereof. An unsaturated alkyl group is one having one or more double bonds or triple bonds. Examples of unsaturated alkyl groups include vinyl, 2-propenyl, crotyl, 2-(butadienyl), ethynyl, 1- and 3-propynyl, 3-butynyl, and the other homologs and isomers. The term "alkyl," unless otherwise noted, is also meant to include those derivatives of alkyl known as "heteroalkyls." Alkyl groups which are limited to hydrocarbon groups are termed "homoalkyl."

The term "alkylene" by itself or as part of another substituent means a divalent radical derived from an alkane, as exemplified by —$CH_2CH_2CH_2CH_2$—, and further includes those groups known as "heteroalkylenes." Typically, an alkyl (or alkylene) group of the present invention will have from 1 to 4 carbon atoms.

A "$C_{1-4}$ alkylene chain" is an alkylene moiety with 1–4 carbons.

The terms "alkoxy," and "alkylthio" (or thioalkoxy) are used in their conventional sense, and refer to those alkyl groups attached to the remainder of the molecule via an oxygen atom, or a sulfur atom, respectively.

A "$C_{1-4}$ alkoxy" group is an alkoxy group with 1–4 carbons.

A "$C_{1-4}$ alkylthio" group is an alkylthio group with 1–4 carbons.

A "compound of formula (I) is present in an amount sufficient to inhibit a MXR transporter," where the efflux of a molecule through a MXR transporter is decreased in the presence of a compound of formula (I) relative to the efflux of that molecule through a MXR transporter in the absence of a compound of formula (I); or where the retention of a molecule in a cell having a MXR transporter is increased in the presence of a compound of formula (I) relative to the retention of that molecule in a cell having a MXR transporter in the absence of a compound of formula (I); or where the cytotoxicity of a molecule is increased in the presence of a compound of formula (I) relative to cytotoxicity of the molecule in the absence of a compound of formula (I).

A "cell has been transfected with a functional MXR gene" when an expression cassette comprising a MXR gene that encodes a functional MXR polypeptide has been introduced into that cell.

The phrase "functional MXR gene" refers to a MXR gene which encodes a MXR transporter with the ability to transport compounds out of a cell. Examples of such compounds include, without limitation, mitoxantrone, topotecan, anthracyclines, SN38 and rhodamine.

The term "expression cassette" refers to a polynucleotide sequence that can direct the expression of a gene.

"Identity" with regard to analogs of MXR refers to refer to two or more amino acid sequences that are the same or have a specified percentage of amino acid residues that are the same, when compared and aligned for maximum correspondence, as measured using the following sequence comparison algorithms. For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Algorithms that are suitable for determining percent sequence identity and sequence similarity are the BLAST and BLAST 2.0 algorithms, which are described in Altschul et al. (1990) *J. Mol. Biol.* 215: 403–410 and Altschuel et al. (1977) *Nucleic Acids Res.* 25: 3389–3402, respectively. Software for performing BLAST analyses is publicly available through the National Center for Biotechnology Information (http://www.ncbi.nlm.nih.gov/).

This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci., U.S.A.* 89:10915 (1989)).

The phrase "modulate the functional effect of said test compound" refers to measuring whether an increase or decrease in the effect of a compound is observed upon the cell. Such functional effects can include, but are not limited to, cytotoxicity of a test compound, efflux of a test compound from a cell, and the retention of a test compound in a cell.

The term "test compound" refers to any compound, artificially or naturally synthesized, or a combination thereof, that is being analyzed. Test compounds can include, but are not limited to, chemotherapeutics, peptides, proteins, hormones, and nucleic acids.

The term "mammal" refers to animals of the class Mammalia. The term "mammal" includes, but is not limited to, a mouse, a rat, a rodent, a primate, a monkey, a human, a rabbit, a sheep, and a pig.

A mammal is "suffering from a cancer" if it contains a cancer, a cancerous cell, a tumorigenic cell, or a tumor.

The term "co-administering" encompasses the administration of two or more compounds simultaneously, or non-simultaneously.

The term "chemotherapeutic" refers to a pharmaceutical, drug, medication, or compound that is used to treat cancer, a cancerous cell, a tumorigenic cell, or a tumor.

The phrase "chemotherapeutic recognized by a MXR transporter" refers to a chemotherapeutic that can be transported out of a cell by a MXR transporter. Examples of such a chemotherapeutic include, but are not limited to, mitoxantrone, topotecan, anthracyclines and SN38.

DETAILED DESCRIPTION

I. Introduction

The present invention provides for methods of inhibiting transport in a cell overexpressing a MXR gene but not a Pgp gene using an acridine derivative. These methods may be useful for the treatment of mammals suffering from a cancer. The emergence of several newly identified members of the ABC transporter family has necessitated the development of antagonists which are able to inhibit more than one transporter. We assessed the ability of the chemosensitizer GF120918 to function as a multispecific antagonist using cytotoxicity assays, rhodamine and calcein efflux assays, and confocal microscopy in cell lines expressing different multidrug resistance transporters.

GF120918 was found to be highly effective at reversing both Pgp-mediated and MXR-mediated multidrug resistance. GF120918 is not an effective inhibitor of MRP. GF120918 was shown to increase the cytotoxicity of both mitoxantrone and topotecan in resistant cells, and to increase the accumulation of mitoxantrone and rhodamine 123 in cells overexpressing both Pgp and the putative new mitoxantrone transporter, MXR. Finally, GF120918 was able to increase the accumulation of rhodamine as seen in flow cytometric analyses. GF120918 therefore appears to fit the paradigm of a multispecific blocker.

II. Isolation of the Gene Encoding MXR or PGP

The genes encoding a human MXR gene (Doyle et al., supra; GenBank Accession Nos: NM 004827 and 4757850) and a human Pgp gene (MDR-1) (Chen et al. (1986), supra; GenBank Accession Nos: AF016535 and AAA59575) have been cloned and overexpressed. A murine MXR has also been cloned and encodes a protein with over 80% amino acid identity to the human MXR (Allen et al. (1999) *Cancer Res.* 59: 4237–4241; GenBank Accession No. M14757). Methods for isolating and expressing MXR or Pgp sequences are described below.

A. General Recombinant DNA Methods

MXR or Pgp polypeptides and nucleic acids are used in the assays described below. For example, recombinant MXR or Pgp nucleic acids can be used to make cells that constitutively express MXR or Pgp. Such polypeptides and nucleic acids can be made using routine techniques in the field of recombinant genetics. Basic texts disclosing the general methods of use in this invention include Sambrook et al., *Molecular Cloning, A Laboratory Manual* (2$^{nd}$ ed. 1989); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides can be chemically synthesized according to the solid phase phosphoramidite triester method first described by Beaucage & Caruthers, *Tetrahedron Letts.* 22:1859–1862 (1981), using an automated synthesizer, as described in Van Devanter et al., *Nucleic Acids Res.*

12:6159–6168 (1984). Purification of oligonucleotides is typically by either native acrylamide gel electrophoresis or by anion-exchange HPLC as described in Pearson & Reanier, *J. Chrom.* 255:137–149 (1983). The sequence of the cloned genes and synthetic oligonucleotides can be verified after cloning using, e.g., the chain termination method for sequencing double-stranded templates of Wallace et al., *Gene* 16:21–26 (1981). Again, as noted above, companies such as Operon Technologies, Inc. provide an inexpensive commercial source for essentially any oligonucleotide.

B. Cloning Methods for the Isolation of Nucleotide Sequences Encoding MXR or Pgp In general, the nucleic acid sequences encoding genes of interest, such as MXR or Pgp and related nucleic acid sequence homologs, are cloned from cDNA and genomic DNA libraries by hybridization with a probe, or isolated using amplification techniques with oligonucleotide primers. Preferably mammalian, more preferably human sequences are used. For example, MXR or Pgp sequences are typically isolated from mammalian nucleic acid (genomic or cDNA) libraries by hybridizing with a nucleic acid probe, such as a probe derived from a MXR sequence (GenBank Accession No: NM 004827) or Pgp sequence (GenBank Accession No: AF016535).

Amplification techniques using primers can also be used to amplify and isolate, e.g., a nucleic acid encoding MXR or Pgp, from DNA or RNA (see, e.g., Dieffenfach & Dveksler, *PCR Primer: A Laboratory Manual* (1995)). These primers can be used, e.g., to amplify either the full length sequence or a probe of one to several hundred nucleotides, which is then used to screen a mammalian library for the full-length nucleic acid of choice. For example, degenerate primer sets for MXR or Pgp sequences can be used to isolate MXR or Pgp nucleic acids. Nucleic acids can also be isolated from expression libraries using antibodies as probes. Such polyclonal or monoclonal antibodies can be raised, e.g., using the sequence of MXR or Pgp.

Polymorphic variants and alleles that are substantially identical to the gene of choice can be isolated using nucleic acid probes, and oligonucleotides under stringent hybridization conditions, by screening libraries. Alternatively, expression libraries can be used to clone, e.g., MXR or Pgp and MXR or Pgp polymorphic variants, interspecies homologs, and alleles, by detecting expressed homologs immunologically with antisera or purified antibodies made against MXR or Pgp, which also recognize and selectively bind to the MXR or Pgp homolog.

To make a cDNA library, one should choose a source that is rich in the mRNA of choice, e.g., for human MXR or Pgp mRNA. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25:263–269 (1983); Sambrook et al., supra; Ausubel et al., supra).

For a genomic library, the DNA is extracted from the tissue and either mechanically sheared or enzymatically digested to yield fragments of about 12-20 kb. The fragments are then separated by gradient centrifugation from undesired sizes and are constructed in non-lambda expression vectors. These vectors are packaged in vitro. Recombinant phage are analyzed by plaque hybridization as described in Benton & Davis, *Science* 196:180–182 (1977). Colony hybridization is carried out as generally described in Grunstein et al., *Proc. Natl. Acad. Sci. USA.*, 72:3961–3965 (1975).

An alternative method of isolating a nucleic acid and its homologs combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of, e.g., MXR or Pgp directly from mRNA, from cDNA, from genomic libraries or cDNA libraries. Degenerate oligonucleotides can be designed to amplify MXR or Pgp homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of MXR or Pgp encoding mRNA in physiological samples, for nucleic acid sequencing, or for other purposes. Genes amplified by the PCR reaction can be purified from agarose gels and cloned into an appropriate vector.

As described above, gene expression of MXR or Pgp can also be analyzed by techniques known in the art, e.g., reverse transcription and PCR amplification of mRNA, isolation of total RNA or poly A+ RNA, northern blotting, dot blotting, in situ hybridization, RNase protection, probing high density oligonucleotides, and the like. All of these techniques are standard in the art.

Synthetic oligonucleotides can be used to construct recombinant genes for use as probes or for expression of protein. This method is performed using a series of overlapping oligonucleotides usually 40–120 bp in length, representing both the sense and non-sense strands of the gene. These DNA fragments are then annealed, ligated and cloned. Alternatively, amplification techniques can be used with precise primers to amplify a specific subsequence of a MXR or a Pgp nucleic acid. The specific subsequence is then ligated into an expression vector.

The nucleic acid encoding the protein of choice is typically cloned into intermediate vectors before transformation into prokaryotic or eukaryotic cells for replication and/or expression. These intermediate vectors are typically prokaryote vectors, e.g., plasmids, or shuttle vectors. Optionally, cells can be transfected with recombinant MXR or Pgp operably linked to a constitutive promoter, to provide higher levels of MXR or Pgp expression in cultured cells.

C. Expression in Prokaryotes and Eukaryotes

To obtain high level expression of a cloned gene or nucleic acid, such as cDNAs encoding MXR or Pgp, one typically subclones MXR or Pgp cDNAs into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al Bacterial expression systems for expressing the MXR or Pgp protein are available in, e.g., *E. coli*, Bacillus sp., and Salmonella (Palva et al., *Gene* 22:229–235 (1983)). Kits for such expression systems are commercially available. Eukaryotic expression systems for mammalian cells, yeast, and insect cells are well known in the art and are also commercially available.

The promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function. The promoter typically cam also include elements that are responsive to transactivation, e.g., hypoxia responsive elements, Gal4 responsive elements, lac repressor responsive elements, and the like. The promoter can be constitutive or inducible, heterologous or homologous.

In addition to the promoter, the expression vector typically contains a transcription unit or expression cassette that contains all the additional elements required for the expression of the nucleic acid in host cells. A typical expression cassette thus contains a promoter operably linked, e.g., to the nucleic acid sequence encoding MXR or Pgp, and signals required for efficient polyadenylation of the transcript, ribosome binding sites, and translation termination. The nucleic acid sequence may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as using a baculovirus vector in insect cells, with a MXR or Pgp encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of protein, which are then purified using standard techniques (see, e.g., Colley et al., *J. Biol. Chem.* 264:17619–17622 (1989); Guide to Protein Purification, in *Methods in Enzymology*, vol. 182 (Deutscher, ed., 1990)). Transformation of eukaryotic and prokaryotic cells are performed according to standard techniques (see, e.g., Morrison, *J. Bact.* 132:349–351 (1977); Clark-Curtiss & Curtiss, *Methods in Enzymology* 101:347–362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

After the expression vector is introduced into the cells, the transfected cells are cultured under conditions favoring expression of a MXR or Pgp protein, which is recovered from the culture using standard techniques identified below.

III. Purification of MXR or Pgp

If necessary, naturally occurring or recombinant proteins can be purified for use in functional assays, e.g., to make antibodies to detect MXR or Pgp. Naturally occurring MXR or Pgp can be purified from cells, cell lines or any other source of a MXR or Pgp homolog. Recombinant MXR or Pgp is purified from any suitable expression system, e.g., by expressing MXR or Pgp in *E. coli* and then purifying the recombinant protein via affinity purification, e.g., by using antibodies that recognize a specific epitope on the protein or on part of the fusion protein, or by using glutathione affinity gel, which binds to GST. In some embodiments, the recombinant protein is a fusion protein, e.g., with GST or Gal4 at the N-terminus.

The protein of choice may be purified to substantial purity by standard techniques, including selective precipitation with such substances as ammonium sulfate; column chromatography, immunopurification methods, and others (see, e.g., Scopes, protein Purification: Principles and Practice (1982); U.S. Pat. No. 4,673,641; Ausubel et al., supra; and Sambrook et al., supra).

A number of procedures can be employed when recombinant protein is being purified. For example, proteins having established molecular adhesion properties can be reversibly fused to MXR or Pgp. With the appropriate ligand, MXR or Pgp can be selectively adsorbed to a purification column and then freed from the column in a relatively pure form. The fused protein is then removed by enzymatic activity. Finally, MXR or Pgp could be purified using immunoaffinity columns.

A. Purification of MXR or Pgp from Recombinant Bacteria

Recombinant proteins are expressed by transformed bacteria in large amounts, typically after promoter induction; but expression can be constitutive. Promoter induction with IPTG is a one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of inclusion bodies. For example, purification of inclusion bodies typically involves the extraction, separation and/or purification of inclusion bodies by disruption of bacterial cells, e.g., by incubation in a buffer of 50 mM Tris/HCl pH 7.5, 50 mM NaCl, 5 mM $MgCl_2$, 1 mM DTT, 0.1 mM ATP, and 1 mM PMSF. The cell suspension can be lysed using 2–3 passages through a French press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. The protein of choice is separated from other bacterial proteins by standard separation techniques, e.g., with Ni-NTA agarose resin.

Alternatively, it is possible to purify the recombinant MXR or Pgp protein from bacteria periplasm. After lysis of the bacteria, when the protein is exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying MXR or Pgp

Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20–30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of the protein, e.g., MXR or Pgp, can be used to isolated it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

The protein of choice can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

IV. Immunological Detection of MXR or Pgp

In addition to the detection of MXR or Pgp genes and gene expression using nucleic acid hybridization technology, one can also use immunoassays to detect MXR or Pgp, e.g., to identify alleles, mutants, polymorphic variants and interspecies homologs of MXR or Pgp. Immunoassays can be used to qualitatively or quantitatively analyze MXR or Pgp, e.g., to detect MXR or Pgp, to measure MXR or Pgp activity, or to identify modulators of MXR or Pgp activity. A general overview of the applicable technology can be found in Harlow and Lane, *Antibodies: A Laboratory Manual* (1988).

A. Antibodies to MXR or Pgp

Methods of producing polyclonal and monoclonal antibodies that react specifically with MXR or Pgp are known to those of skill in the art (see, e.g., Coligan, *Current Protocols in Immunology* (1991); Harlow & Lane, supra; Goding, *Monoclonal Antibodies: Principles and Practice* ($2^{nd}$ ed. 1986); and Kohler & Milstein, *Nature* 256:495–497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275–1281 (1989); Ward et al., *Nature* 341:544–546 (1989)). In addition, as noted above, many companies, such as BMA Biomedicals, Ltd., HTI Bio-products, and the like, provide the commercial service of making an antibody to essentially any peptide.

A number of MXR or Pgp comprising immunogens may be used to produce antibodies specifically reactive with MXR or Pgp. For example, recombinant MXR or Pgp, or antigenic fragments thereof, are isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. To improve reproducibility, an inbred strain of mice (e.g., BALB/C mice) can be immunized to make the antibody; however, standard animals (mice, rabbits, etc.) used to make antibodies are immunized with the protein using a standard adjuvant, such as Freund's adjuvant, and a standard immunization protocol (see Harlow & Lane, supra). The animal's immune response to the immunogen preparation is monitored by taking test bleeds and determining the titer of reactivity to the protein of choice. When appropriately high titers of antibody to the immunogen are obtained, blood is collected from the animal and antisera are prepared. Further fractionation of the antisera to enrich for antibodies reactive to the protein can be done if desired (see Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, *Eur. J. Immunol.* 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246:1275–1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-MXR or Pgp proteins or even other related proteins, e.g. from other organisms, using a competitive binding immunoassay. Specific polyclonal antisera and monoclonal antibodies will usually bind with $K_D$ of at least about 0.1 mM, more usually at least about 1 $\mu$M, preferably at least about 0.1 $\mu$M or better, and most preferably, 0.01 $\mu$M or better.

Once MXR or Pgp specific antibodies are available, these proteins can be detected by a variety of immunoassay methods. For a review of immunological and immunoassay procedures, see *Basic and Clinical Immunology* (Stites & Terr eds., $7^{th}$ ed. 1991). Moreover, the immunoassays of the present invention can be performed in any of several configurations, which are reviewed extensively in *Enzyme Immunoassay* (Maggio, ed., 1980); and Harlow & Lane, supra.

B. Immunological Binding Assays

MXR or Pgp can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case MXR or Pgp, or antigenic fragments thereof). The antibody may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled MXR or Pgp polypeptide or a labeled anti-MXR or Pgp antibody. Alternatively, the labeling agent may be a third moiety, such a secondary antibody, that specifically binds to the antibody/antigen complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.* 111:1401–1406 (1973); Akerstrom et al., *J. Immunol.* 135:2589–2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non-competitive Assay Formats

Immunoassays for detecting MXR or Pgp in samples may be either competitive or noncompetitive. Noncompetitive immunoassays are assays in which the amount of antigen is directly measured. In one preferred "sandwich" assay, for example, the anti-antigen antibodies can be bound directly to a solid substrate on which they are immobilized. These immobilized antibodies then capture antigen present in the test sample. Antigen thus immobilized is then bound by a labeling agent, such as a second antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of MXR or Pgp present in the sample is measured indirectly by measuring the amount of a known, added (exogenous) antigen displaced (competed away) from an anti-antigen antibody by the unknown antigen present in a sample. In one competitive assay, a known amount of antigen is added to a sample and the sample is then contacted with an antibody that specifically binds to the antigen. The amount of exogenous antigen bound to the antibody is inversely proportional to the concentration of antigen present in the sample. In a particularly preferred embodiment, the antibody is immobilized on a solid substrate. The amount of antigen bound to the antibody may be determined either by measuring the amount of antigen present in an antigen/antibody complex, or alternatively by measuring the amount of remaining uncomplexed protein. The amount of antigen may be detected by providing a labeled antigen molecule.

A hapten inhibition assay is another preferred competitive assay. In this assay the known antigen is immobilized on a solid substrate. A known amount of anti-antigen antibody is added to the sample, and the sample is then contacted with the immobilized antigen. The amount of anti-antigen antibody bound to the known immobilized antigen is inversely proportional to the amount of antigen present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Other Assay Formats

Western blot (immunoblot) analysis is used to detect and quantify the presence of MXR or Pgp in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind MXR or Pgp. The anti-antigen antibodies specifically bind to the antigen on the solid support. These antibodies may be directly labeled or alternatively may be subsequently detected using labeled antibodies (e.g., labeled sheep anti-mouse antibodies) that specifically bind to the anti-antigen antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34–41 (1986)).

Reduction of Non-specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize a specific protein, or secondary antibodies that recognize antibodies to the specific protein.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple calorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

V. Selection and Identification of Cells that Overexpress MXR but Do Not Overexpress Pgp Cells overexpressing the MXR gene but not the Pgp gene can be obtained in a number of ways. One method is the selection of a drug-resistant cell line from a parental cell line. The cell line is subjected to increasing amounts of a drug, such as mitoxantrone, and the cells resistant to the increasing amount of drug are continued in culture.

A. Selection of Drug Resistant Cell Lines

Drug resistant cell lines are selected by exposing the cell line of interest to increasing amounts of the drug of interest. Cell lines that overexpress MXR but do not overexpress Pgp have previously been isolated by exposing cell lines to increasing concentrations of topotecan, mitoxantrone, or doxorubicin (Chen et al. (1990) *J. Biol. Chem.* 265: 10073–10080; Doyle et al., supra; Allen et al. supra; Miyake et al. supra).

Alternatively, a mouse cell line can be constructed that lacks the MRP and Pgp gene, and overexpresses a MXR gene using the method of Allen et al. supra. Briefly, embryo and fibroblast cells lines were isolated from knockout mice that had the genotype Mdr1a$^{-/-}$ Mdr1b$^{-/-}$ Mrp1$^{-/-}$ (Allen et al.). Sublines resistant to topotecan, mitoxantrone or doxorubicin were selected by increasing the respective drug concentration over a period of 4–8 months.

B. Transfection of Cells with a MXR Expression Cassette.

Another method for creating a cell line that overexpresses a MXR gene but does not overexpress a Pgp gene is to transfect a cell that does not overexpress the Pgp gene with an expression cassette encoding a MXR gene (Doyle et al., supra). Methods for obtaining a MXR gene and for creating an expression cassette for expression in eukaryotic cells are described herein and are well known in the art (See Ausubel et al., supra). For example, MCF-7 breast cancer cells when transfected with a vector expressing an MXR gene become resistant to mitoxantrone, doxorubicin, and daunorubicin (Doyle et al., supra).

C. Identification of Cells Which Overexpress a MXR Gene but Do Not Overexpress a Pgp Gene.

Cells which overexpress the MXR gene but do not overexpress the Pgp gene can be identified in a number of ways. Typically a MXR overexpressing cell, that does not overexpress a Pgp, will be resistant to drugs such as mitoxantrone, topotecan, anthracyclines, and SN38, but will be sensitive to vinca alkaloids, taxanes and VP-16. Thus, one of skill in the art could analyze a cell or tumor to determine whether the cell possessed that characteristic through cytotoxicity, efflux, or retention assays. Alternatively, one of skill in the art could prepare protein extracts from the cell of interest and perform a Western blot using anti-Pgp antibodies (Lee et al., supra) and anti-MXR antibodies. Methods for creating such antibodies are known in the art (Ausubel et al., supra). A cell line that overexpresses the MXR gene but does not overexpress a Pgp gene (e.g., MCF-7 AdVp) will have a MXR immunoreactive band that is more predominant than in the parental cell line (e.g., MCF-7) or a non-tumorigenic/non-cancerous cell of the same type of cell (e.g., breast cell). Conversely, the Pgp immunoreactive band, if any, in the cell line that overexpresses the MXR gene but does not overexpress the Pgp gene will not be more prominent than a band, if any, if the parental cell line or non-tumorigenic/non-cancerous cell of the same type of cell.

Alternatively, RNA can be isolated from the cell of interest and probed in a Northern blot (Ausubel et al., supra) or subjected to RT-PCR (Innis et al., supra). Similar to the Western blot analysis, a cell line, tumor, or cancer cell that overexpresses a MXR gene will have a more predominant band on a Northern blot or a more predominant PCR product than a cell which does not overexpress a MXR gene. Conversely, the Pgp PCR product (if any) or Northern blot band (if any) would not be more predominant that the parental cell line or non-cancerous cell type.

VI. Assays of Transporter Activity

The ability of the acridine derivative (a compound of formula I) to inhibit or modulate activity of the MXR transporter can be determined by a variety of assays known in the art. Typically, the acridine derivative's ability to modulate the transport of a molecule which is normally transported by the MXR transporter is assayed. The acridine derivatives do not appear to inhibit the MRP transporter. To determine effectiveness of an acridine derivative, the assays need to be performed on a cell that overexpresses the MXR gene but does not overexpress the Pgp gene. The MXR transporters function as ATP-dependent cytotoxin efflux pumps. Thus, if a MXR transporter is known to reduce the cytoplasmic concentration of a particular drug, the efflux of the drug can be determined in first in the absence and then in the presence of an acridine derivative. Alternatively, cytotoxicity or drug retention/accumulation assays can be performed. Examples of these methods are described below.

A. Cytotoxicity Assays.

A variety of cytotoxicity assays are known in the art. Briefly, cells are treated in the presence of an agent, drug, or chemotherapeutic. Then the percentage of cells that are living after exposure to the agent are determined using an assay. One example of a cytotoxicity assay is the sulforhodamine staining assay of Skehan et al. (1990) *J. Natl. Cancer Inst.* 82: 1107–1112). Briefly, cells are incubated in the presence of an agent, e.g., mitoxantrone or topotecan. After the incubation the cells are fixed in TCA and stained with sulforhodamine B. The absorbance of cells can be read on a plate reader at 540 nm.

B. Fluorescent Compound Accumulation Assays

Cells can be assayed for MXR or Pgp transport activity by incubating the cells in the presence of a fluorescent substrate. The amount of fluorescent substrate in the cell can be assayed using fluorescence activated cell sorting (FACS) analysis. Two examples of these kinds of assays are the rhodamine and calcein efflux assay (Lee et al. (1994) *Mol. Pharmacol.* 46: 627–638; Versantvoort et al. (1995) *Int. J. Cancer* 63: 855–862.). Rhodamine is a substrate for both Pgp and MXR, while calcein AM is only a substrate for Pgp. Suspensions of logarithmic phase cells were obtained from tissue culture flasks by trypsinization and transferred into round-bottom 96-well plates. The cells were resuspended in media containing rhodamine 123 or calcein AM. After incubation, the cells are washed and resuspended in rhodamine-free media for an efflux period. After the efflux period, the cells are washed and placed on ice. A FACS flow cytometer is then used to measure rhodamine 123 or calcein fluorescence after a 530 nm bandpass filter. Propidium idodide staining is used to exclude cells that are dead.

C. Labeled Drug Accumulation Assay

Similar to the fluorescent compound accumulation assay, cells can be assayed for their ability to accumulate a radiolabeled compound (Fojo et al., (1985) *Cancer Res.* 45: 3002–3007; U.S. Pat. No. 5,369,009). For example, cells can be assayed for their ability to intracellularly accumulate $^3$H-daunomycin (DuPont) (Fojo et al., supra; U.S. Pat. No. 5,369,009). Cells are incubated in $^3$H-daunomycin and then the cells are centrifuged to separate the cells from the medium. The cell pellet is solubilized in 1 M NaOH at 60° C. overnight. Then, glacial acetic acid is added and mixed with the solubilized cell pellet. A scintillation counter is then used to measure the amount of radioactivity in the sample.

D. Mitoxantronefluorescence Assay

The cellular accumulation of mitoxantrone can be determined using flow cytometry (Allen et al.). Excitation is performed at 633 nm and a 661 nm band-pass filter is used to detect emission. Mitoxantrone is added to cells and allowed to incubate. To stop the assay, the cells are put on ice. Cells are trypsinized on ice and assayed using flow cytometry to determine the amount of mitoxantrone in the cells.

VII. Screening Assay for Modulation of the Functional Effect of a Test Compound The methods of the present invention are also useful for screening the ability of an acridine derivative (e.g., GF120918) to modulate the functional effect of a test compound on a cell that overexpresses a MXR gene but does not overexpress a Pgp gene. Test compounds can essentially be any compound, and in some embodiments is a chemotherapeutic. Such an assay is useful for determining whether an acridine derivative has the ability to prevent a cell from becoming resistant to a test compound or to reverse a cell's resistance to a test compound. The functional effect(s) of a test compound on a cell can include, but are not limited to, cytotoxicity, efflux of a compound from a cell, and the retention of the compound in a cell. Assays for cytotoxicity, efflux, and retention are described herein and are known in the art. To perform the assay, cells overexpressing a MXR gene but not a Pgp gene are incubated with a test compound in the absence and presence of an acridine derivative. If the cells become more sensitive to a functional effect of the test compound, e.g., cytotoxicity, in the presence of the acridine derivative, then the test compound is a candidate to be co-administered with an acridine derivative to a mammal suffering from a cancer producing tumor cells that overexpresses a MXR gene but not a Pgp gene.

VIII. Pharmaceutical Compositions and Administration

The compositions containing the present acridine derivatives, or a cocktail thereof (i.e., with other molecules), can be administered for therapeutic purposes. Methods for synthesizing and formulating acridine derivatives useful in the present invention are described in WO 92/12132, supra and U.S. Pat. No. 5,604,237, supra.

A. Pharmaceutical Compositions

The compositions for administration may be in the form of a solution, suspension, tablets, pill, capsule, powder, gel, cream, lotion, ointment, aerosol or the like. Pharmaceutical compositions for administering GF120918A, the hydrochloride salt of GF120918, are described in WO 96/11007. In a preferred embodiment, the compositions for administration comprise a solution of the acridine derivative dissolved in a pharmaceutically acceptable carrier, preferably an aqueous carrier. A variety of aqueous carriers can be used, e.g., buffeted saline and the like. These solutions are sterile and generally free of undesirable matter. These compositions may be sterilized by conventional, well known sterilization techniques. In certain embodiments, the acridine derivatives are provided in powder form.

The acridine derivatives may be combined with conventional excipient, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of the acridine derivative in these formulations can vary widely, and will be selected primarily based on fluid volumes, viscosities, body weight and the like in accordance with the particular mode of administration selected and the patient's needs.

B. Administration and Dosage

Mammals suffering from a cancer that overexpresses a MXR gene but not a Pgp gene are candidates for being treated with an acridine derivative (e.g., GF120918 or GF120918A) and a chemotherapeutic. Briefly, a chemotherapeutic recognized by the MXR transporter is co-administered with an acridine derivative (e.g., GF120918 or GF 120918A) to a mammal suffering from a cancer that overexpresses a MXR gene but which does not overexpress a Pgp gene. Examples of chemotherapeutics recognized by the MXR transporter include, but are not limited to, mitoxantrone, topotecan, anthracyclines and SN38. The types of cancers that overexpress a MXR gene but not a Pgp gene can include, but are not limited to, lung cancer, a colon cancer, breast cancer, prostate cancer, acute lymphocytic leukemia, non-Hodgkin's lymphoma, and ovarian cancer.

In therapeutic applications, the acridine derivatives and the chemotherapeutic compositions are administered to a mammal suffering from a cancer or condition in an amount sufficient to fully or partially restore sensitivity or fully or partially prevent resistance to one or more chemotherapeutics, or combinations thereof. An amount adequate to accomplish this is defined as a "effective amount." Amounts effective for this use will depend upon the severity of the condition to be treated and the general state of the patient's health.

Effective amounts can range from about 0.01 micrograms to about 100 mg/kg body weight, and preferably from about 10 micrograms to about 50 mg/kg body weight, such 0.05, 0.07, 0.09, 0.1, 0.5, 0.7, 0.9, 1, 2, 5, 10, 20, 25, 30, 40, 45, or 50 mg/kg. In general, doses of the acridine derivative for treatment of an adult human will preferably be in the range of about 1 mg to about 10 g per day, more preferably in the range from about 10 mg to about 1 g per day, still more preferably in the range from about 25 mg to about 750 mg per day.

It is understood that the dosage of an acridine derivatives of the present invention will be dependent upon the age, sex, health, and weight of the recipient, kind of concurrent treatment, if any, frequency of treatment, and the nature of the effect desired. The ranges of effective doses provided herein are not intended to limit the inventors and represent preferred dose ranges. The most preferred dosage will be tailored to the individual subject, as is understood and determinable by one of skill in the art, without undue experimentation. It is contemplated that the compounds will be administered under the guidance of a physician, who will determine the exact dosages, monitor the progress of the treatment, and determine whether a given administration is successful and sufficient, or whether subsequent administrations are needed.

The pharmaceutical composition or medium that comprises an acridine derivative is administered orally, parentally, enterically, gastrically, topically, subcutaneously, rectally, locally or systemically. For example, the compounds can be injected into the bloodstream using a cannula or catheter; the vein or artery is selected to maximize delivery of cells to the affected tissue(s). Actual methods for preparing parentally administrable compositions will be known or apparent to those skilled in the art and are described in more detail in such publications as *Remington's Pharmaceutical Science*, 15th ed., Mack Publishing Company, Easton, Pennsylvania (1980). It is recognized that the acridine derivatives described above, when administered orally, should be protected from digestion. This is typically accomplished either by complexing the acridine derivative with a composition to render it resistant to acidic and enzymatic hydrolysis.

The concentration of compounds to be administered at a given time and to a given patient will vary from 0.1 µg–100 mg and preferably 0.1–10 mg per day per patient. The dosage and mode of administration may be chosen to achieve and optionally maintain a local concentration in fluids that contact the target cells of about 0.001–50 µg/ml, preferably 0.1–10 µg/ml. Dosages from 0.1 up to about 100 mg per patient per day may be used, particularly when the drug is administered to a secluded site and not into the blood stream, such as into a body cavity or into a lumen of an organ. Substantially higher dosages are possible in topical administration.

Single or multiple administrations of the compositions may be necessary depending on the dosage and frequency as required and tolerated by the patient. In any event, the composition should provide a sufficient quantity of the peptides of this invention to effectively treat the patient.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. The following examples are not offered to limit the claimed invention. All publications, patents, and patent applications cited herein are hereby incorporated by reference in their entirety for all purposes.

Materials and Cell Lines

The following materials and cell lines were used in the examples below. GF120918 was obtained from Glaxo Pharmaceuticals (Research Triangle Park, N.C.). Mitoxantrone, topotecan, and rhodamine 123 were obtained from Sigma Chemical Co. (St. Louis, Mo.). Calcein AM was obtained from Molecular Probes (Eugene, Oreg.).

The cell lines used were the S1 colon cancer cell line, the MCF-7 breast cancer cell line and several derivative sublines which have been selected in chemotherapeutic drugs for acquired drug resistance. The human colon carcinoma cell line, S1, and its mitoxantrone and bisantrene resistant sublines, S1-M1-3.2 and S1-B1-20, were kindly provided by Dr. Lee M. Greenberger (Wyeth-Ayerst) (Zhang et al. (1994) *Oncol. Res.* 6: 291–301; Rabindran et al. (1998) *Cancer Res.* 58: 5850–5858). The S1-M1-80 subline was selected from S1-M1-3.2 cells in gradually increased concentrations of mitoxantrone for the studies presented here and are maintained in 80 µM mitoxantrone. The S1-B1-20 subline is maintained in 20 µM bisantrene.

The S1 parental cells express low endogenous levels of Pgp. The S1-B1-20 cells overexpress Pgp (Zhang et al. (1994) *Oncol. Res.* 6: 291–301), while the S1-M1-80 cells do not overexpress Pgp or MRP (data not shown) and express high levels of a mitoxantrone transporter (Miyake et al. (1999) *Cancer Res*.59: 8–13). The MRP over-expressing human breast cancer subline, MCF-7/VP, kindly provided by Dr. Ken Cowan, was maintained in 4 µM VP-16 and used in preliminary studies (Schneider et al. (1994) *Cancer Res.* 54: 152–158). MCF-7 parental cells were used as a control in several experiments.

The S1 colon cancer cell lines were cultured in RPMI 1640 (Biofluids Inc., Rockville, Md.) and MCF-7 cell lines were cultured in IMEM (Biofluids Inc., Rockville, Md.). Both RPMI and IMEM were supplemented with 10% fetal bovine serum (Life Technologies, Gaithersburg, Md.), 2 mM glutamine, 100 units/ml penicillin, and 100 µg/ml streptomycin (Biofluids Inc., Rockville, Md.). Experiments were carried out with cells cultured 7–10 days out of drug.

Example 1

In Vitro Cytotoxicity Assay

Reversal of resistance was determined in cytotoxicity assays using the sulforhodamine staining (Skehan et al. (1990) *J. Natl. Cancer Inst.* 82: 1107–1112). Briefly, cells were harvested and seeded at a density of 2000 cells/well for the colon cancer lines and 4000 cells/well for the breast cancer cell lines in flat-bottom 96-well plates. The cells were incubated for 24 h at 37° C. to allow attachment prior to addition of the drugs. Mitoxantrone and topotecan at various concentrations were added to the cells with or without the reversal agent and were incubated at 37° C. in a fully humidified atmosphere of 5% $CO_2$ for 96 h. Each concentration was tested in triplicate and the controls were done in replicates of eight. Results are representative of from three to six experiments. Rigorous attention to the concentration and density of plated cells was required in order to achieve reproducible cytotoxicity results for mitoxantrone.

After incubation, the cells were fixed in TCA and stained with sulforhodamine B (SRB) solution (0.4% wt/vol in 1% acetic acid) (Sigma Chemical, St Louis, Mo.). Optical densities were read on a Bio-Rad plate reader (Hercules, Calif.) at an absorbance of 540 nm. The $IC_{50}$ (concentration at which 50% of the growth is inhibited) was determined for each drug.

The cytotoxicity of GF120918 was initially tested in the resistant sublines. No evidence of cross-resistance in the resistant sublines was observed. The $IC_{50}$ for GF120918 alone in each of the cell lines was 15.2, 3.6, 2.5, 40 and 7.5 µM for S1 parental, S1-B1-20, S1-M1-80, MCF-7 parental and MCF-7/VP cell lines, respectively.

Figure 1D:
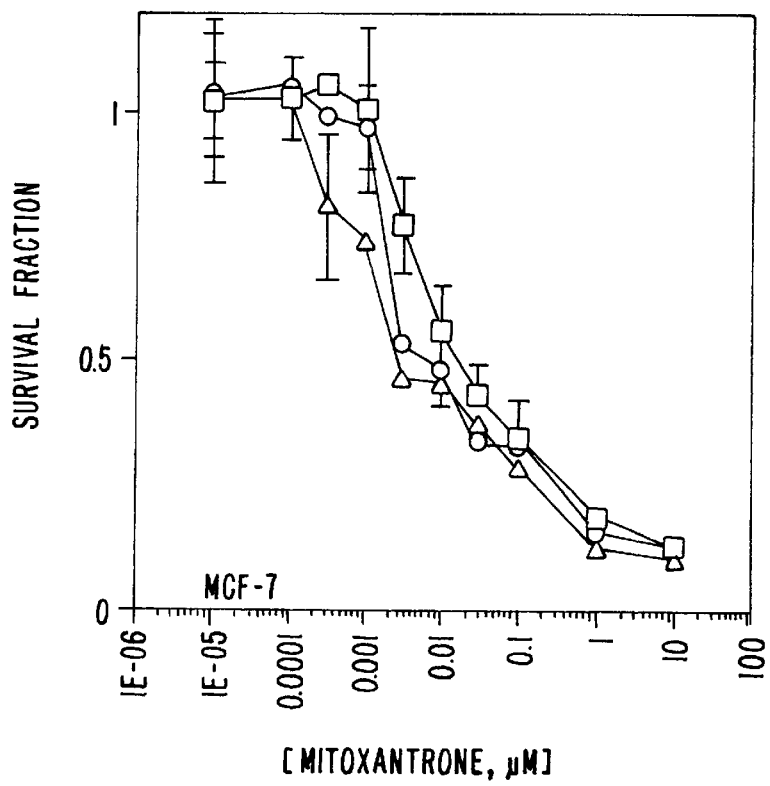

Next, the $IC_{50}$s of mitoxantrone and topotecan were assessed with or without GF120918 in the different cell lines. FIGS. 1A, B, and C show the results of GF120918 reversal of mitoxantrone resistance in S1, S1-B1-20, and S1-M1-80 cells, respectively. MCF-7 cells (FIG. 1D) are included as a control cell line expressing no Pgp. The equation:

$$DMF = \frac{IC_{50}(-GF)}{IC_{50}(+GF)}$$

was used to calculate the dose modifying factor (DMF), comparing the $IC_{50}$ in the presence (+GF) or absence (−GF) of GF120918. GF120918 at 1 µM results in a 31-fold sensitization of Pgp-expressing S1-B1-20 cells, while the S1-M1-80 cells expressing MXR, a putative mitoxantrone transporter, are sensitized 1850-fold.

We also examined the dependence of mitoxantrone reversal on the concentration of GF120918. A substantial decrease in the reversing ability of GF120918 was observed when the concentration of GF120918 was decreased from 1 µM to 0.5 µM. The DMF for mitoxantrone in the S1-M1-80 cells decreased from 1850 to 141, suggesting a steep dose response relationship for this agent in the MXR expressing cells. The results of the cytotoxicity assays in the resistant cells with GF120918 at 0.5 and 1 µM for both mitoxantrone and topotecan are recorded in Table 1.

TABLE 1

IC$_{50}$ values for mitoxantrone and topotecan with or without GG918 at a concentration of 0.5 $\mu$M or 1.0 $\mu$M.

|  | IC$_{50}$ ($\mu$M) | RR | +0.5 $\mu$M GF120918 IC$_{50}$ ($\mu$M) | DMF[1] | +1.0 $\mu$M GF120918 IC$_{50}$ ($\mu$M) | DMF |
|---|---|---|---|---|---|---|
| Mitoxantrone |  |  |  |  |  |  |
| MCF-7 | 0.025 ± 0.019 | — | 0.0057 ± 0.0073 | 4.4 | 0.0056 ± 0.0081 | 4.4 |
| S1 | 0.0062 ± 0.0047 | — | 0.0053 ± 0.0043 | 1.2 | 0.0052 ± 0.0044 | 1.2 |
| S1-B1-20 | 0.41 ± 0.61 | 66 | 0.015 ± 0.0056 | 27 | 0.013 ± 0.0066 | 31 |
| S1-M1-80 | 222 ± 101 | 35806 | 1.57 ± 0.95 | 141 | 0.12 ± 0.11 | 1850 |
| Topetecan |  |  |  |  |  |  |
| MCF-7 | ND[2] | — | ND | — | ND | — |
| S1 | 0.036 ± 0.0085 | — | 0.034 | 1.0 | 0.025 ± 0.007 | 1.4 |
| S1-M1-20 | 0.160 ± 0.05 | 4.4 | 0.040 | 4 | 0.027 ± 0.005 | 5.9 |
| S1-M1-80 | 12.02 ± 5.0 | 334 | 2.0 | 6 | 0.52 ± 0.30 | 23 |

[1]The Dose Modifying Factor (DMF) is defined as the IC$_{50}$ for the chemotherapy drug without GG918 divided by the IC$_{50}$ with GG918.
[2]Not Determined There was little reversal effect in the S1-B1-20 cells or in the S1-M1-80 cells with GF120918 when used in combination with topotecan, and higher concentrations of GF120918 had little additional effect on the DMF (Table 1). For the Pgp-expressing subline, this may be due to the fact that topotecan is a relatively poor substrate. The resistance to topotecan is only 4.4-fold in the S1-B1-20 cells. For the MXR-expressing S1-M1-80 cells, topotecan appears to be a better substrate, with a relative resistance of 334-fold. These numbers can be contrasted with the relative resistance to paclitaxel, 200-fold for S1-B1-20 and 1.5-fold for S1-M1-80 (data not shown). GF120918 at 1M sensitized the S1-M1-80 cells 23-fold, but the IC$_{50}$ at 520 $\mu$M did not reflect complete sensitization (The IC$_{50}$ for SI cells was 36 nM). GF120918, in agreement with a previous report, was found to be ineffective in reversing MRP-mediated resistance as determined by cytotoxicity reversal studies with etoposide and MRP-overexpressing MCF-7 VP-16 cells (data not shown) (Germann et al. (1997) Anticancer Drugs 8: 141–55)

Example 2

Efflux Assays

The rhodamine and calcein efflux assays were performed as previously described with minor modifications (Lee et al. (1994) Mol. Pharmacol. 46: 627–638; Versantvoort et al. (1995) Int. J. Cancer 63: 855–862.) Suspensions of logarithmic phase cells were obtained from tissue culture flasks by trypsinization and transferred into round-bottom 96-well plates. The cells were resuspended in complete media (phenol-red free IMEM with 10% FCS) alone, or complete media with 0.5 $\mu$g/ml rhodamine 123 or 0.25 $\mu$M calcein AM with or without GF120918 and incubated at 37° C. in 5% CO$_2$ for 30 minutes. After incubation, the cells were washed once in Dulbecco's phosphate buffered saline (DPBS) and placed on ice in the dark or were resuspended in rhodamine-free complete media with or without GF120918 and incubated at 37° C. in 5% CO$_2$ for a one hour efflux period. After the efflux period, the cells were washed with DPBS and placed on ice. A FACSort flow cytometer (Becton Dickinson, San Jose, Calif.) with a 488-nm argon laser was used to analyze the samples. Rhodamine 123 or calcein fluorescence was collected after a 530 nm bandpass filter. A minimum of 10,000 events was collected per sample and the samples were gated on forward scatter versus side scatter to exclude clumps and debris; dead cells were excluded based on propidium iodide staining.

Rhodamine Efflux Assay

The cytotoxicity data presented above suggested that GF120918 is effective at inhibiting at least 2 mechanisms of drug transport. To provide confirmation, rhodamine efflux assays were performed. Rhodamine 123 is a fluorescent dye which has been shown to be a substrate for Pgp and appears to be a substrate for the putative mitoxantrone transporter encoded by MXR (Lee et al. (1997) J. Cell Biochem. 65: 513–526). After an accumulation and efflux period, rhodamine fluorescence was quantitated by flow cytometric analysis. The results are depicted in FIG. 2. GF120918 was shown not to be fluorescent at the concentrations examined. PSC 833, a cyclosporin-D analog, was used as a positive control for Pgp antagonism.

Figure 2A:
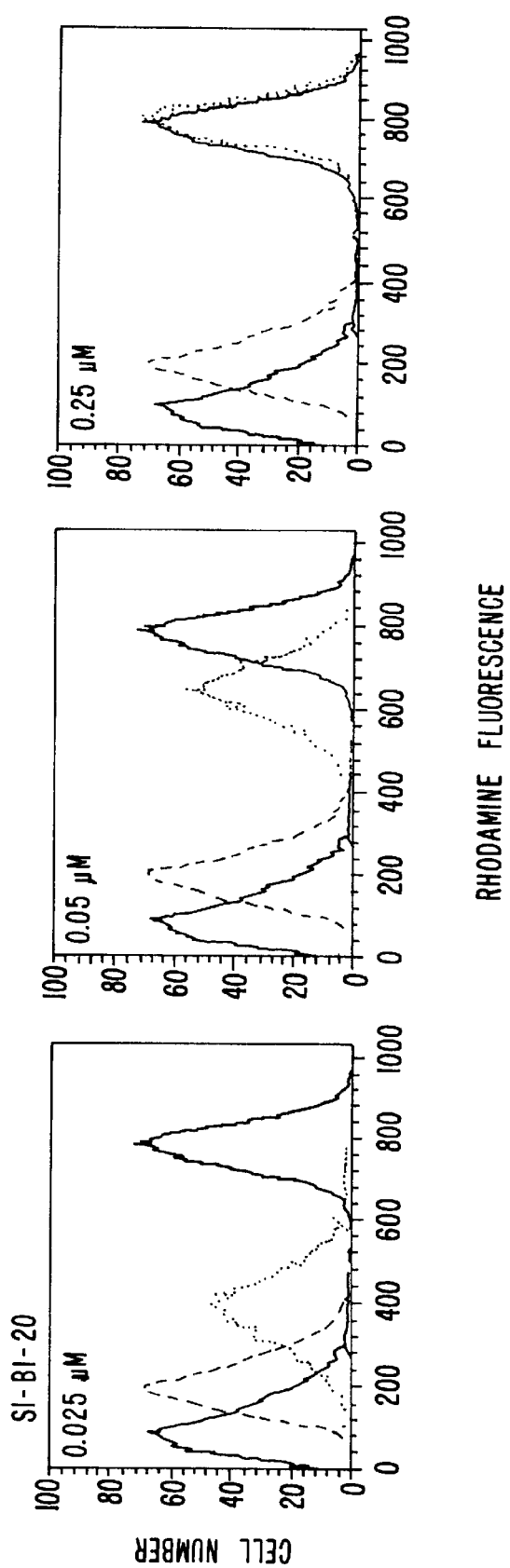
FIG. 2 demonstrates rhodamine efflux in drug resistant cell lines. Blank histogram (solid line): cells incubated in media alone. Efflux histogram: cells incubated 30 min in media containing 0.5 μg/ml rhodamine 123 without (dashed line) or with (dotted line) GF120918 at the indicated concentration, washed, and incubated 60 min in rhodamine-free media without or with GF120918 again at the indicated concentration. PSC 833 histogram (heavy solid line): cells incubated in 3 μg/ml PSC 833 during both accumulation and efflux periods. PSC 833 was only used in the Pgp-expressing lines as it is not an effective antagonist for MXR. Panel A: Rhodamine efflux in Pgp-overexpressing S1-B1-20 cells. Panel B: Rhodamine Efflux in S1-M1-80 cells expressing the mitoxantrone transporter, MXR. Panel C: Rhodamine efflux in S1 parental cells which express a low endogenous level of Pgp. Panel D: Rhodamine efflux in MCF-7 parental cells.
Figure 2B:
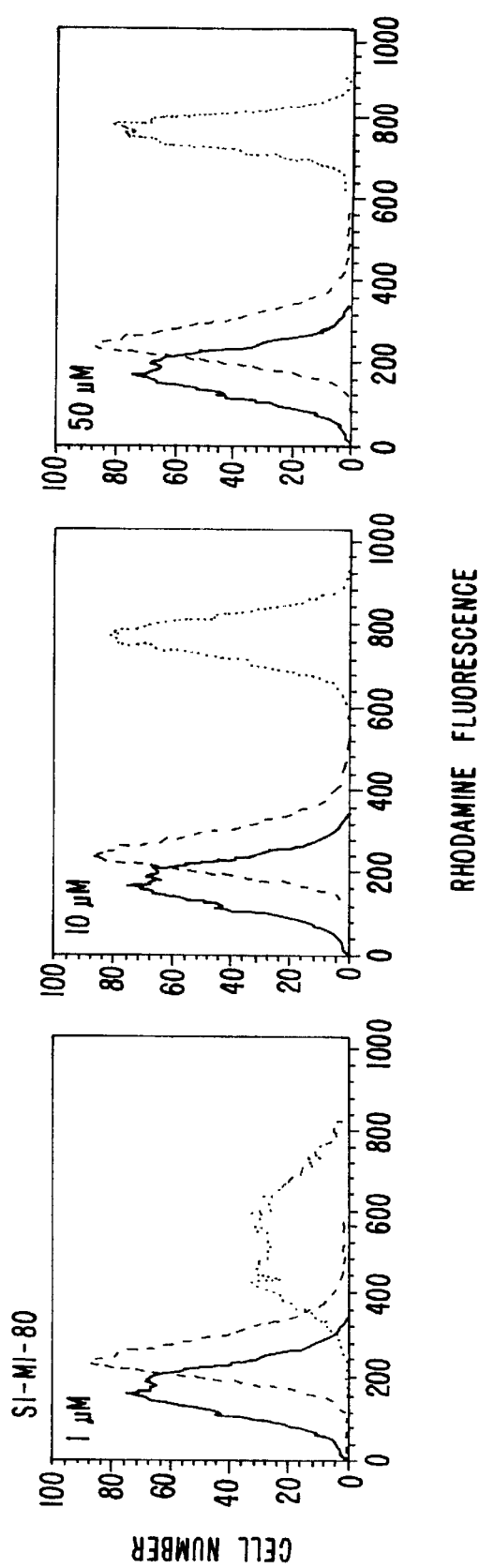
Figures 2C, 2D:
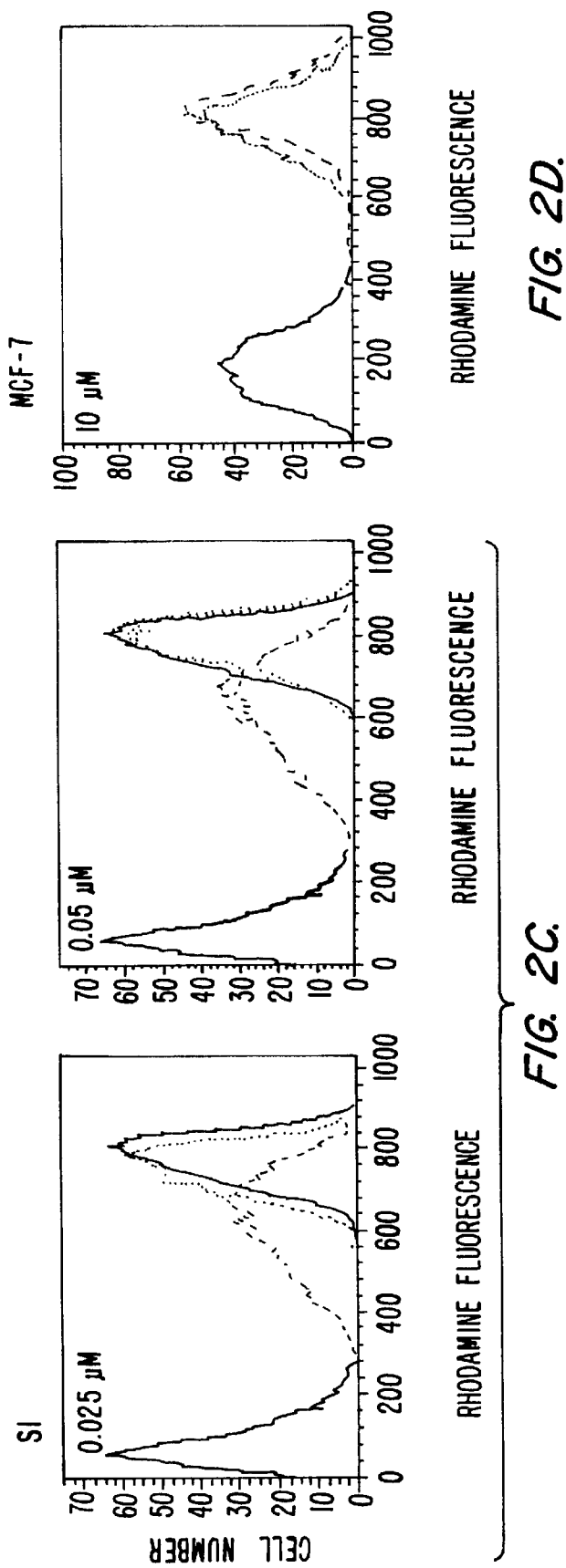

GF120918 was most potent in the Pgp-expressing S1-B1-20 cells, as seen in FIG. 2A. At a GF120918 concentration of 0.25 $\mu$M, rhodamine fluorescence following both accumulation and efflux was indistinguishable from that with 3 $\mu$g/mL PSC 833. Further, at concentrations as low as 25 $\mu$M to 50 nM of GF120918, there was some evidence of inhibition of rhodamine efflux in the Pgp-expressing cells.

Panel B demonstrates that GF120918 also inhibits rhodamine efflux from the mitoxantrone-resistant S1-M1-80 cells. Much higher concentrations of GF120918 were required relative to the Pgp-expressing cells. Although an effect was observed at 1 $\mu$M GF120918, 10 $\mu$M was required for complete inhibition of rhodamine efflux. In S1 parental cells, PSC 833 and GF120918 both resulted in a small increase in rhodamine accumulation and a decrease in efflux due to the low basal level of Pgp in S1 parental cells. No effect of GF120918 is seen in MCF-7 parental cells (Panel D).

Calcein Efflux Assay

Calcein AM can be used to detect both Pgp and MRP-mediated efflux. Calcein permeates the cell in neutral form as an acetomethoxyester, calcein AM. Esterase activity cleaves the AM group leaving calcein as a fluorescent organic anion. Both calcein-AM and calcein have been shown to be substrates for MRP; only calcein-AM is a substrate for Pgp (Feller et al. (1995) FEBS Lett. 368: 385–388). Calcein is readily effluxed in the MRP-overexpressing MCF-7/VP cells. Consistent with the failure of GF120918 to sensitize the MRP-expressing cells to VP-16, reversal studies using calcein efflux detected by FACS analysis demonstrated only slight reversal of MRP-mediated calcein efflux at 25 μM (data not shown). GF120918 was able to block efflux of calcein AM from Pgp-expressing S1-B1-20 cells. The GF120918 concentration which gave half-maximal inhibition of Pgp as measured by its ability to inhibit efflux of calcein-AM, $K_{i,GF120918}$, was calculated to be 50 nM. This value was independent of the substrate concentration, showing that GF120918 is a non-competitive inhibitor of Pgp. Neither calcein AM nor calcein appeared to be a substrate for MXR.

In the flow cytometric analysis with rhodamine, there was a dose-dependent response to GF120918 in the S1-B1-20 and S1-M1-80 cells. Rhodamine 123 efflux in S1-B 1-20 cells was decreased at GF120918 concentrations as low as 25 to 50 nM, with 250 nM giving complete inhibition of rhodamine efflux. Efficient blocking of rhodamine efflux in S1-M1-80 was achieved only at 10 μM and higher. In contrast, in the in vitro cytotoxicity assay, while not achieving full reversal, it was found that concentrations 10 to 20 times lower were effective in increasing sensitivity to mitoxantrone. It was also observed that much higher concentrations were required to increase mitoxantrone accumulation by confocal microscopy, relative to the cytotoxicity assay. These observations may be explained by differing affinities of the compounds for the transporters, by the duration of the assays or by metabolism of the drugs involved. GF120918 could be more efficient in the longer-term assays if it interferes with the intracellular trafficking of mitoxantrone which is required for metabolism.

While the activity of GF120918 was tested in highly selected cells, the degree of resistance in human cancers due to these transporters is probably much lower. Thus the level of potency these compounds need to have an effect on cells expressing MXR may be significantly less in the in vivo situation. GF120918 is able to reverse resistance or increase drug accumulation in cells expressing both Pgp (S1-B1-20) and the newly described multidrug resistance transporter, MXR (S1-M1-80). It was most potent against Pgp, but also achieved significant modulation of MXR. GF120918 thus fits the paradigm of a multispecific blocker.

Example 3

Confocal Microscopy

Cells were seeded in 35 mm glass-bottom microwell dishes (MatTek Corporation, Ashland, Mass.) at a density of 4000 cells/dish and incubated for 48 hours in phenol red-free IMEM supplemented with 10% fetal calf serum. Subsequently, the medium was removed and 1.5 ml IMEM with the appropriate concentration of GF120918 was added. Following a 40 min preincubation, 1.5 ml IMEM with GF120918 at the appropriate concentrations with 1 μM mitoxantrone was added and accumulation was allowed for 30 minutes to one hour at 37° C. in a fully humidified atmosphere of 5% $CO_2$ in air. The cells were analyzed using a Zeiss LSM 410 confocal laser scanning microscope equipped with a 15 mV argon laser exciting mitoxantrone at 568 nm. Emitted light passed through a 590 nm long-pass filter.

Since it has been reported that cell lines expressing non-Pgp, non-MRP mediated resistance may have compartmentalization as a mechanism of resistance (Dietel et al. (1990) *Cancer Res*. 50: 6100–6106) we examined the effect of GF120918 on the fluorescence of mitoxantrone by confocal microscopy. A punctuate, perinuclear, staining pattern was observed in all S1 cells and resistant sublines at comparable levels, suggesting that the accumulation of mitoxantrone in a vesicular compartment is an intrinsic phenotype in these cells. Unless a greater rate of vesicle formation and extrusion were present, an identical pattern of vesicles in the parental or resistant sublines would imply that vesicular accumulation is not a major contribution to the resistance phenotype.

In the absence of GF120918, the drug-sensitive S1 parental cells had the highest intracellular drug levels and intense nuclear staining with mitoxantrone (data not shown). Mitoxantrone levels were decreased in both the P-glycoprotein overexpressing S1-B1-20 cells and the MXR-expressing S1-M1-80 cells (data not shown). Reduced rhodamine accumulation was also observed in the S1-B1-20 cells and the S1-M1-80 cells (data not shown).

Treatment with 0.4 μM GF120918 during mitoxantrone incubation increased mitoxantrone fluorescence in the resistant P-glycoprotein overexpressing S1-B1-20 subline to a level comparable to that of the parental line (data not shown). The effect of GF120918 was less marked on the S1-M1-80 cells, which showed a preexisting punctuate staining pattern for mitoxantrone due to the chronic exposure to 80 μM mitoxantrone. Likewise, rhodamine 123 accumulation is enhanced in the S1-B1-20 cells with 0.4 μM GF120918, although not in the S1-M1-80 line.

At a higher concentration of GF120918, the S1-M1-80 cell line showed some increase in mitoxantrone accumulation with nuclear staining, although not to the same level as the S1 parental or S1-B1-20 cells (data not shown). In contrast, the rhodamine 123 accumulation defect in the S1-M1-80 cells was reversed at 2 μM GF120918 which would suggest that the resistance mechanism in this cell line has differential affinities for mitoxantrone and rhodamine 123 (data not shown). Full reversal of the rhodamine accumulation defect in the S1-M1-80 cells occurred at 10 μM GF120918. At still higher GF120918 levels, such as 10 μM, and 50 μM, the mitoxantrone level in the S1-M1-80 cells increased further, to reach the saturating levels observed in the S1 parental and S1-B1-20 cells with profound nuclear staining, indicating that full reversal had been achieved (data not shown).

Example 4

For the purpose of testing the ability of a compound of formula (I) or a salt or solvate thereof (e.g., GF120918, GF120918A, etc.) to reverse MXR in a mouse model system and to examine the efficacy of treating cancers that overexpress a MXR gene, but do not overexpress a Pgp gene, three cell lines were selected in mitoxantrone: A549 (lung carcinoma; American Type Culture Collection, Manassas, Va.), NCI-H460 (lung carcinoma; American Type Culture Collection), SF295 (human glioblastoma; National Cancer Institute (NCI)). These cell lines were chosen because they expressed low, but detectable levels of MXR overexpression among a 60 cell line panel used by a NCI drug screen. The cell lines were selected in the presence of 10 nM mitoxantrone. The cell lines that were stable and overexpressed MXR and were designated A549/MX10, NCI-H460/MX10, and SF295/MX10. These resistant sublines (e.g., NCI-H460/MX10) ought to provide a more clinically relevant model than cell lines selected with very high levels of mitoxantrone (e.g., S1-M1-80 or MCF-7 AdVp) to achieve high levels of MXR expression. Studies with Pgp have indicated that it is important to use cell lines with levels of transporter expression which are within the range of MXR overexpression exhibited in the clinical arena, in order to have an accurate assessment of the degree of reversal which could be expected from Pgp inhibition in clinical trials.

The mitoxantrone-resistant cells lines were then initially evaluated along side the parental cell line for their ability to grow as xenografts in nude mice. The following cell lines were implanted: A549, A549/MX10, NCI-H460, NCI-H460/MX10, SF295, and SF295/MX10. The status of the growth of the six cell lines implanted subcutaneously as xenografts in nude mice ($10^7$ cells per mouse) was as follows:

| Cell line | Growth as Xenograft in Nude Mice |
|---|---|
| A549 parent | Not tested |
| A549/MX10 | Did not grow |
| NCI-H460 parent | Grew well |
| NCI-H460/MX10 | Grew, but more slowly than NCI-460 parent |
| SF295 parent | Did not grow |
| SF295/MX10 | Did not grow |

Because the NCI-460 parental control grew well in addition to the NCI-H460/MX10, this cell line will be used in a mouse model to study whether a compound of formula (I) or a salt or solvate thereof (e.g., GF120918, GF120918A, etc.) can inhibit the growth of NCI-460/MX10 tumors when administered in conjunction with a chemotherapeutic agent (e.g., mitoxantrone, CPT-11 (Irinotecan), topotecan, etc.).

For the in vivo mouse xenograft tumor reversal studies, a chemotherapeutic will be analyzed for its ability to treat (e.g., shrink the size, reduce spread of, etc.) the NCI-H460/MX10 xenograft tumors in the presence as compared to the absence of a compound of formula (I) or a salt or solvate thereof (e.g., GF120918, GF120918A, etc.). A compound of formula (I) that will be tested is GF120918. A candidate chemotherapeutic that will be tested is CPT-11 (Irinotecan). Other chemotherapeutics such as mitoxantrone and topotecan will also be tested. The chemotherapeutic and GF120918 can be delivered using any method known in the art, such as intravenous, intraperitoneal, and oral delivery. The GF120918 will be given at a range of doses to different mice, which can include 1, 5, 10, 30, 50, 100, 300 mg/kg/dose. Administration of GF120918 to mice has no apparent toxic effects when administered orally at single doses up to 300 mg/kg (U.S. Pat. No. 6,604,237). Intravenous dosages of CPT-11 at 90, 60, 40, and 27 mg/kg/dose will each be initially tested for efficacy. Higher and lower dosages of GF120918 or the chemotherapeutic being co-administered may also be tested depending on the initial results. The chemotherapeutic will be administered on day 1, day 5 and day 9. The GF120918 will be administered for 3 to 4 doses immediately before and then every 4 hours after the dose of the chemotherapeutic, e.g., CPT-11.

The efficacy of the dosages and treatment regimens will also be evaluated by performing a surrogate assay using serum drawn from the test mice, and applied to the MXR-overexpressing cell line, S1-M1-80. This surrogate assay will be used confirm that the GF1209189 treated-mice have GF120918 serum levels that are sufficient to overcome MXR-mediated drug transport. The surrogate assays can involve applying the serum to an MXR-overexpressing cell line in vitro, in which mitoxantrone or BODIPY-prazosin (Molecular Probes, Inc., Eugene, Oreg.) is incubated prior to assay by flow cytometry.

What is claimed is:

1. A method of inhibiting a MXR transporter in a cell overexpressing a MXR gene but not overexpressing a Pgp gene comprising:

contacting said cell, which overexpresses a MXR gene, but does not overexpress a Pgp gene, with a compound of formula (I):

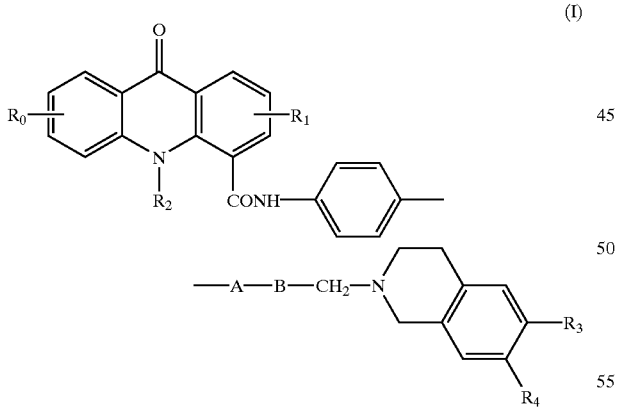

(I)

wherein $R_0$ represents a hydrogen or halogen atom, or a $C_{1-4}$ alkyl, $C_{1-4}$ alkoxy, $C_{1-4}$ alkylthio, amino, or nitro group;
$R_1$ represents a hydrogen or a halogen atom, or a $C_{1-4}$ alkyl, $C_{1-4}$ alkoxy, or $C_{1-4}$ alkylthio group;
$R_2$ represents a hydrogen or a $C_{1-4}$ alkyl group;
A represents an oxygen or a sulfur atom or a bond;
B represents an unsubstituted $C_{1-4}$ alkylene chain
$R_3$ and $R_4$ each independently represents a $C_{1-4}$ alkoxy group;

or salts and solvates thereof; and
wherein said compound of formula (I) is present in an amount sufficient to inhibit a MXR transporter.

2. The method as claimed in claim 1, wherein said cell has been transfected with a functional MXR gene.

3. The method as claimed in claim 1, wherein said cell contains a functional MXR gene placed in an expression cassette.

4. The method as claimed in claim 1, wherein said compound is N-{4-[2-1,2,3,4-tetrahydro-6,7-dimethoxy-2-isoquinolinyl)-ethyl]-phenyl}-9,10-dihydro-5-methoxy-9-oxo-4-acridine carboxamide or salts and solvates thereof.

5. A method of assaying the modulation of the functional effect of a test compound on a cell, that overexpresses a MXR gene but not a Pgp gene, by a compound as recited in claim 1, comprising the steps of:

contacting said test compound with said cells which overexpress a MXR gene and do not overexpress a Pgp gene, in the presence and absence of said compound as recited in claim 1 or its salts and solvates thereof; and measuring the ability of said compound as recited in claim 1 and its salts and solvates thereof, to modulate the functional effect of said test compound.

6. The method of claim 5, wherein said test compound is selected from the group consisting of: mitoxantrone, an anthracycline, topotecan, SN38, CPT-11, doxorubicin, and daunorubicin.

7. The method as claimed in claim 5, where said compound as recited in claim 1 is N-{4-[2-1,2,3,4-tetrahydro-6,7-dimethoxy-2-isoquinolinyl)-ethyl]-phenyl}-9,10-dihydro-5-methoxy-9-oxo-4-acridine carboxamide or salts and solvates thereof.

8. The method as claimed in claim 5, wherein said cell has been transfected with a MXR gene.

9. The method as claimed in claim 5, wherein said cell contains a functional MXR gene placed in an expression cassette.

10. The method as claimed in claim 5, wherein said cell has been transfected with a MXR gene and wherein said compound of claim 1 is N-{4-[2-1,2,3,4-tetrahydro-6,7-dimethoxy-2-isoquinolinyl)-ethyl]-phenyl}-9,10-dihydro-5-methoxy-9-oxo-4-acridine carboxamide or salts and solvates thereof.

11. A method of treatment of a mammal which is suffering from a cancer that overexpresses the MXR gene but does not overexpress a Pgp gene comprising:

co-administering to said mammal a chemotherapeutic which is recognized by a MXR transporter and an effective amount of the compound as recited in claim 1 and salts or solvates thereof.

12. The method of claim 11 wherein said compound as recited in claim 1 is N-{4-[2-1,2,3,4-tetrahydro-6,7-dimethoxy-2-isoquinolinyl)-ethyl]-phenyl}-9,10-dihydro-5-methoxy-9-oxo-4-acridine carboxamide, or its salts and solvates thereof.

13. The method of claim 11, wherein said chemotherapeutic is selected from the group consisting of: mitoxantrone, an anthracycline, topotecan, SN38, CPT-11, doxorubicin, and daunorubicin.

14. The method of claim 11, wherein said cancer is a lung cancer, a colon cancer, breast cancer, prostate cancer, acute lymphocytic leukemia, non-Hodgkin's lymphoma, or a ovarian cancer.

* * * * *

SEQUENCE LISTING

<160> NUMBER OF SEQ ID NOS: 2

<210> SEQ ID NO 1
<211> LENGTH: 655
<212> TYPE: PRT
<213> ORGANISM: Homo sapiens
<220> FEATURE:
<223> OTHER INFORMATION: human mitoxanthrone resistance (MXR)/BRCP/ABCP
      protein

<400> SEQUENCE: 1

Met Ser Ser Ser Asn Val Glu Val Phe Ile Pro Val Ser Gln Gly Asn
 1               5                   10                  15

Thr Asn Gly Phe Pro Ala Thr Val Ser Asn Asp Leu Lys Ala Phe Thr
            20                  25                  30

Glu Gly Ala Val Leu Ser Phe His Asn Ile Cys Tyr Arg Val Lys Leu
        35                  40                  45

Lys Ser Gly Phe Leu Pro Cys Arg Lys Pro Val Glu Lys Glu Ile Leu
    50                  55                  60

Ser Asn Ile Asn Gly Ile Met Lys Pro Gly Leu Asn Ala Ile Leu Gly
65                  70                  75                  80

Pro Thr Gly Gly Gly Lys Ser Ser Leu Leu Asp Val Leu Ala Ala Arg
                85                  90                  95

Lys Asp Pro Ser Gly Leu Ser Gly Asp Val Leu Ile Asn Gly Ala Pro
            100                 105                 110

Arg Pro Ala Asn Phe Lys Cys Asn Ser Gly Tyr Val Val Gln Asp Asp
        115                 120                 125

```
Val Val Met Gly Thr Leu Thr Val Arg Glu Asn Leu Gln Phe Ser Ala
    130                 135                 140

Ala Leu Arg Leu Ala Thr Thr Met Thr Asn His Glu Lys Asn Glu Arg
145                 150                 155                 160

Ile Asn Arg Val Ile Glu Glu Leu Gly Leu Asp Lys Val Ala Asp Ser
                165                 170                 175

Lys Val Gly Thr Gln Phe Ile Arg Gly Val Ser Gly Gly Glu Arg Lys
            180                 185                 190

Arg Thr Ser Ile Gly Met Glu Leu Ile Thr Asp Pro Ser Ile Leu Ser
        195                 200                 205

Leu Asp Glu Pro Thr Thr Gly Leu Asp Ser Ser Thr Ala Asn Ala Val
    210                 215                 220

Leu Leu Leu Lys Arg Met Ser Lys Gln Arg Thr Ile Ile Phe
225                 230                 235                 240

Ser Ile His Gln Pro Arg Tyr Ser Ile Phe Lys Leu Phe Asp Ser Leu
                245                 250                 255

Thr Leu Leu Ala Ser Gly Arg Leu Met Phe His Gly Pro Ala Gln Glu
            260                 265                 270

Ala Leu Gly Tyr Phe Glu Ser Ala Gly Tyr His Cys Glu Ala Tyr Asn
        275                 280                 285

Asn Pro Ala Asp Phe Phe Leu Asp Ile Ile Asn Gly Asp Ser Thr Ala
    290                 295                 300

Val Ala Leu Asn Arg Glu Glu Asp Phe Lys Ala Thr Glu Ile Ile Glu
305                 310                 315                 320

Pro Ser Lys Gln Asp Lys Pro Leu Ile Glu Lys Leu Ala Glu Ile Tyr
                325                 330                 335

Val Asn Ser Ser Phe Tyr Lys Glu Thr Lys Ala Glu Leu His Gln Leu
            340                 345                 350

Ser Gly Gly Glu Lys Lys Lys Ile Thr Val Phe Lys Glu Ile Ser
        355                 360                 365

Tyr Thr Thr Ser Phe Cys His Gln Leu Arg Trp Val Ser Lys Arg Ser
    370                 375                 380

Phe Lys Asn Leu Leu Gly Asn Pro Gln Ala Ser Ile Ala Gln Ile Ile
385                 390                 395                 400

Val Thr Val Val Leu Gly Leu Val Ile Gly Ala Ile Tyr Phe Gly Leu
                405                 410                 415

Lys Asn Asp Ser Thr Gly Ile Gln Asn Arg Ala Gly Val Leu Phe Phe
            420                 425                 430

Leu Thr Thr Asn Gln Cys Phe Ser Ser Val Ser Ala Val Glu Leu Phe
        435                 440                 445

Val Val Glu Lys Lys Leu Phe Ile His Glu Tyr Ile Ser Gly Tyr Tyr
    450                 455                 460

Arg Val Ser Ser Tyr Phe Leu Gly Lys Leu Leu Ser Asp Leu Leu Pro
465                 470                 475                 480

Met Arg Met Leu Pro Ser Ile Ile Phe Thr Cys Ile Val Tyr Phe Met
                485                 490                 495

Leu Gly Leu Lys Pro Lys Ala Asp Ala Phe Phe Val Met Met Phe Thr
            500                 505                 510

Leu Met Met Val Ala Tyr Ser Ala Ser Ser Met Ala Leu Ala Ile Ala
        515                 520                 525

Ala Gly Gln Ser Val Val Ser Val Ala Thr Leu Leu Met Thr Ile Cys
    530                 535                 540

Phe Val Phe Met Met Ile Phe Ser Gly Leu Leu Val Asn Leu Thr Thr
```

```
545                 550                 555                 560

Ile Ala Ser Trp Leu Ser Trp Leu Gln Tyr Phe Ser Ile Pro Arg Tyr
                565                 570                 575

Gly Phe Thr Ala Leu Gln His Asn Glu Phe Leu Gly Gln Asn Phe Cys
                580                 585                 590

Pro Gly Leu Asn Ala Thr Gly Asn Asn Pro Cys Asn Tyr Ala Thr Cys
            595                 600                 605

Thr Gly Glu Glu Tyr Leu Val Lys Gln Gly Ile Asp Leu Ser Pro Trp
        610                 615                 620

Gly Leu Trp Lys Asn His Val Ala Leu Ala Cys Met Ile Val Ile Phe
625                 630                 635                 640

Leu Thr Ile Ala Tyr Leu Lys Leu Leu Phe Leu Lys Lys Tyr Ser
                645                 650                 655

<210> SEQ ID NO 2
<211> LENGTH: 1280
<212> TYPE: PRT
<213> ORGANISM: Homo sapiens
<220> FEATURE:
<223> OTHER INFORMATION: human P-glycoprotein (Pgp)/multi-drug
      resistance 1 (Mdr-1) ATP-binding cassette (ABC transporter)
      protein

<400> SEQUENCE: 2

Met Asp Leu Glu Gly Asp Arg Asn Gly Gly Ala Lys Lys Lys Asn Phe
 1               5                  10                  15

Phe Lys Leu Asn Asn Lys Ser Glu Lys Asp Lys Lys Glu Lys Lys Pro
                20                  25                  30

Thr Val Ser Val Phe Ser Met Phe Arg Tyr Ser Asn Trp Leu Asp Lys
            35                  40                  45

Leu Tyr Met Val Val Gly Thr Leu Ala Ala Ile Ile His Gly Ala Gly
        50                  55                  60

Leu Pro Leu Met Met Leu Val Phe Gly Glu Met Thr Asp Ile Phe Ala
65                  70                  75                  80

Asn Ala Gly Asn Leu Glu Asp Leu Met Ser Asn Ile Thr Asn Arg Ser
                85                  90                  95

Asp Ile Asn Asp Thr Gly Phe Phe Met Asn Leu Glu Glu Asp Met Thr
            100                 105                 110

Arg Tyr Ala Tyr Tyr Tyr Ser Gly Ile Gly Ala Gly Val Leu Val Ala
        115                 120                 125

Ala Tyr Ile Gln Val Ser Phe Trp Cys Leu Ala Ala Gly Arg Gln Ile
130                 135                 140

His Lys Ile Arg Lys Gln Phe Phe His Ala Ile Met Arg Gln Glu Ile
145                 150                 155                 160

Gly Trp Phe Asp Val His Asp Val Gly Glu Leu Asn Thr Arg Leu Thr
                165                 170                 175

Asp Asp Val Ser Lys Ile Asn Glu Val Ile Gly Asp Lys Ile Gly Met
            180                 185                 190

Phe Phe Gln Ser Met Ala Thr Phe Phe Thr Gly Phe Ile Val Gly Phe
        195                 200                 205

Thr Arg Gly Trp Lys Leu Thr Leu Val Ile Leu Ala Ile Ser Pro Val
    210                 215                 220

Leu Gly Leu Ser Ala Ala Val Trp Ala Lys Ile Leu Ser Ser Phe Thr
225                 230                 235                 240

Asp Lys Glu Leu Leu Ala Tyr Ala Lys Ala Gly Ala Val Ala Glu Glu
                245                 250                 255
```

-continued

```
Val Leu Ala Ala Ile Arg Thr Val Ile Ala Phe Gly Gly Gln Lys Lys
            260                 265                 270
Glu Leu Glu Arg Tyr Asn Lys Asn Leu Glu Glu Ala Lys Arg Ile Gly
        275                 280                 285
Ile Lys Lys Ala Ile Thr Ala Asn Ile Ser Ile Gly Ala Ala Phe Leu
    290                 295                 300
Leu Ile Tyr Ala Ser Tyr Ala Leu Ala Phe Trp Tyr Gly Thr Thr Leu
305                 310                 315                 320
Val Leu Ser Gly Glu Tyr Ser Ile Gly Gln Val Leu Thr Val Phe Phe
                325                 330                 335
Ser Val Leu Ile Gly Ala Phe Ser Val Gly Gln Ala Ser Pro Ser Ile
            340                 345                 350
Glu Ala Phe Ala Asn Ala Arg Gly Ala Ala Tyr Glu Ile Phe Lys Ile
        355                 360                 365
Ile Asp Asn Lys Pro Ser Ile Asp Ser Tyr Ser Lys Ser Gly His Lys
    370                 375                 380
Pro Asp Asn Ile Lys Gly Asn Leu Glu Phe Arg Asn Val His Phe Ser
385                 390                 395                 400
Tyr Pro Ser Arg Lys Glu Val Lys Ile Leu Lys Gly Leu Asn Leu Lys
                405                 410                 415
Val Gln Ser Gly Gln Thr Val Ala Leu Val Gly Asn Ser Gly Cys Gly
            420                 425                 430
Lys Ser Thr Thr Val Gln Leu Met Gln Arg Leu Tyr Asp Pro Thr Glu
        435                 440                 445
Gly Met Val Ser Val Asp Gly Gln Asp Ile Arg Thr Ile Asn Val Arg
    450                 455                 460
Phe Leu Arg Glu Ile Ile Gly Val Val Ser Gln Glu Pro Val Leu Phe
465                 470                 475                 480
Ala Thr Thr Ile Ala Glu Asn Ile Arg Tyr Gly Arg Glu Asn Val Thr
                485                 490                 495
Met Asp Glu Ile Glu Lys Ala Val Lys Glu Ala Asn Ala Tyr Asp Phe
            500                 505                 510
Ile Met Lys Leu Pro His Lys Phe Asp Thr Leu Val Gly Glu Arg Gly
        515                 520                 525
Ala Gln Leu Ser Gly Gly Gln Lys Gln Arg Ile Ala Ile Ala Arg Ala
    530                 535                 540
Leu Val Arg Asn Pro Lys Ile Leu Leu Leu Asp Glu Ala Thr Ser Ala
545                 550                 555                 560
Leu Asp Thr Glu Ser Glu Ala Val Val Gln Val Ala Leu Asp Lys Ala
                565                 570                 575
Arg Lys Gly Arg Thr Thr Ile Val Ile Ala His Arg Leu Ser Thr Val
            580                 585                 590
Arg Asn Ala Asp Val Ile Ala Gly Phe Asp Asp Gly Val Ile Val Glu
        595                 600                 605
Lys Gly Asn His Asp Glu Leu Met Lys Glu Lys Gly Ile Tyr Phe Lys
    610                 615                 620
Leu Val Thr Met Gln Thr Ala Gly Asn Glu Val Glu Leu Glu Asn Ala
625                 630                 635                 640
Ala Asp Glu Ser Lys Ser Glu Ile Asp Ala Leu Glu Met Ser Ser Asn
                645                 650                 655
Asp Ser Arg Ser Ser Leu Ile Arg Lys Arg Ser Thr Arg Ser Val
            660                 665                 670
```

```
Arg Gly Ser Gln Ala Gln Asp Arg Lys Leu Ser Thr Lys Glu Ala Leu
            675                 680                 685

Asp Glu Ser Ile Pro Pro Val Ser Phe Trp Arg Ile Met Lys Leu Asn
            690                 695                 700

Leu Thr Glu Trp Pro Tyr Phe Val Val Gly Val Phe Cys Ala Ile Ile
705                 710                 715                 720

Asn Gly Gly Leu Gln Pro Ala Phe Ala Ile Phe Ser Lys Ile Ile
            725                 730                 735

Gly Val Phe Thr Arg Ile Asp Asp Pro Glu Thr Lys Arg Gln Asn Ser
            740                 745                 750

Asn Leu Phe Ser Leu Leu Phe Leu Ala Leu Gly Ile Ile Ser Phe Ile
            755                 760                 765

Thr Phe Phe Leu Gln Gly Phe Thr Phe Gly Lys Ala Gly Glu Ile Leu
            770                 775                 780

Thr Lys Arg Leu Arg Tyr Met Val Phe Arg Ser Met Leu Arg Gln Asp
785                 790                 795                 800

Val Ser Trp Phe Asp Asp Pro Lys Asn Thr Thr Gly Ala Leu Thr Thr
            805                 810                 815

Arg Leu Ala Asn Asp Ala Ala Gln Val Lys Gly Ala Ile Gly Ser Arg
            820                 825                 830

Leu Ala Val Ile Thr Gln Asn Ile Ala Asn Leu Gly Thr Gly Ile Ile
            835                 840                 845

Ile Ser Phe Ile Tyr Gly Trp Gln Leu Thr Leu Leu Leu Leu Ala Ile
            850                 855                 860

Val Pro Ile Ile Ala Ile Ala Gly Val Val Glu Met Lys Met Leu Ser
865                 870                 875                 880

Gly Gln Ala Leu Lys Asp Lys Lys Glu Leu Glu Gly Ala Gly Lys Ile
            885                 890                 895

Ala Thr Glu Ala Ile Glu Asn Phe Arg Thr Val Val Ser Leu Thr Gln
            900                 905                 910

Glu Gln Lys Phe Glu His Met Tyr Ala Gln Ser Leu Gln Val Pro Tyr
            915                 920                 925

Arg Asn Ser Leu Arg Lys Ala His Ile Phe Gly Ile Thr Phe Ser Phe
930                 935                 940

Thr Gln Ala Met Met Tyr Phe Ser Tyr Ala Gly Cys Phe Arg Phe Gly
945                 950                 955                 960

Ala Tyr Leu Val Ala His Lys Leu Met Ser Phe Glu Asp Val Leu Leu
            965                 970                 975

Val Phe Ser Ala Val Val Phe Gly Ala Met Ala Val Gly Gln Val Ser
            980                 985                 990

Ser Phe Ala Pro Asp Tyr Ala Lys Ala Lys Ile Ser Ala Ala His Ile
            995                 1000                1005

Ile Met Ile Ile Glu Lys Thr Pro Leu Ile Asp Ser Tyr Ser Thr Glu
     1010                1015                1020

Gly Leu Met Pro Asn Thr Leu Glu Gly Asn Val Thr Phe Gly Glu Val
1025                1030                1035                1040

Val Phe Asn Tyr Pro Thr Arg Pro Asp Ile Pro Val Leu Gln Gly Leu
            1045                1050                1055

Ser Leu Glu Val Lys Lys Gly Thr Leu Ala Leu Val Gly Ser Ser
            1060                1065                1070

Gly Cys Gly Lys Ser Thr Val Val Gln Leu Leu Glu Arg Phe Tyr Asp
     1075                1080                1085

Pro Leu Ala Gly Lys Val Leu Leu Asp Gly Lys Glu Ile Lys Arg Leu
```

```
                1090              1095                1100
Asn Val Gln Trp Leu Arg Ala His Leu Gly Ile Val Ser Gln Glu Pro
1105                 1110                1115               1120

Ile Leu Phe Asp Cys Ser Ile Ala Glu Asn Ile Ala Tyr Gly Asp Asn
                1125               1130                1135

Ser Arg Val Val Ser Gln Glu Glu Ile Val Arg Ala Ala Lys Glu Ala
                1140                1145                1150

Asn Ile His Ala Phe Ile Glu Ser Leu Pro Asn Lys Tyr Ser Thr Lys
           1155                1160                1165

Val Gly Asp Lys Gly Thr Gln Leu Ser Gly Gly Gln Lys Gln Arg Ile
    1170               1175                1180

Ala Ile Ala Arg Ala Leu Val Arg Gln Pro His Ile Leu Leu Leu Asp
1185                 1190                1195                1200

Glu Ala Thr Ser Ala Leu Asp Thr Glu Ser Glu Lys Val Val Gln Glu
                1205                1210                1215

Ala Leu Asp Lys Ala Arg Glu Gly Arg Thr Cys Ile Val Ile Ala His
                1220                1225                1230

Arg Leu Ser Thr Ile Gln Asn Ala Asp Leu Ile Val Val Phe Gln Asn
           1235                1240                1245

Gly Arg Val Lys Glu His Gly Thr His Gln Gln Leu Leu Ala Gln Lys
    1250                1255                1260

Gly Ile Tyr Phe Ser Met Val Ser Val Gln Ala Gly Thr Lys Arg Gln
1265                 1270                1275                1280
```